(12) United States Patent
Pouliot

(10) Patent No.: US 10,515,390 B2
(45) Date of Patent: Dec. 24, 2019

(54) METHOD AND SYSTEM FOR DATA OPTIMIZATION

(71) Applicant: NIO USA, Inc., San Jose, CA (US)

(72) Inventor: Christopher F. Pouliot, San Mateo, CA (US)

(73) Assignee: NIO USA, Inc., San Jose, CA (US)

( * ) Notice: Subject to any disclaimer, the term of this patent is extended or adjusted under 35 U.S.C. 154(b) by 266 days.

(21) Appl. No.: 15/393,010

(22) Filed: Dec. 28, 2016

(65) Prior Publication Data

US 2018/0144369 A1    May 24, 2018

Related U.S. Application Data

(60) Provisional application No. 62/424,976, filed on Nov. 21, 2016.

(51) Int. Cl.
   *G06Q 30/00*     (2012.01)
   *B60W 40/09*     (2012.01)
   (Continued)

(52) U.S. Cl.
   CPC .......... *G06Q 30/0266* (2013.01); *A61B 5/01* (2013.01); *A61B 5/024* (2013.01); *A61B 5/08* (2013.01);
   (Continued)

(58) Field of Classification Search
   None
   See application file for complete search history.

(56) References Cited

U.S. PATENT DOCUMENTS

| | | | |
|---|---|---|---|
| 4,361,202 | A | 11/1982 | Minovitch |
| 4,476,954 | A | 10/1984 | Johnson et al. |

(Continued)

FOREIGN PATENT DOCUMENTS

| | | |
|---|---|---|
| CN | 1417755 | 5/2003 |
| CN | 1847817 | 10/2006 |

(Continued)

OTHER PUBLICATIONS

U.S. Appl. No. 61/567,962, filed Dec. 7, 2011, Baarman et al.
(Continued)

*Primary Examiner* — Matthew T Sittner
(74) *Attorney, Agent, or Firm* — Sheridan Ross P.C.

(57) ABSTRACT

Embodiments can provide an intelligent vehicle that determines that the vehicle interior comprises multiple occupants; identifies the occupants; based on the driving behavior of the vehicle, creates a composite occupant profile associated with the group of plural occupants, the composite occupant profile comprising the identities of the plural occupants and group preferences for various vendor products or services; and, based on the composite occupant profile and received inputs from a user interface, an automatic vehicle location system, and a plurality of sensors in the vehicle, performs one or more actions, such as: (a) proposing one or more vendor products or services for the group of occupants; (b) publishing the vendor products or services selected by the group of occupants, via a social network, to associated or selected associates of the occupants in the group; and (c) presenting advertisement information from a vendor server associated with the proposed or selected vendor products or services to one or more of the occupants in the group.

16 Claims, 11 Drawing Sheets

(51) Int. Cl.
| | | |
|---|---|---|
| *B60W 50/08* | (2012.01) | |
| *B60W 10/18* | (2012.01) | |
| *B60W 10/20* | (2006.01) | |
| *G08G 1/16* | (2006.01) | |
| *B60W 10/04* | (2006.01) | |
| *B60W 40/04* | (2006.01) | |
| *B60W 40/08* | (2012.01) | |
| *B60W 40/105* | (2012.01) | |
| *G01S 13/87* | (2006.01) | |
| *G01S 15/02* | (2006.01) | |
| *B62D 15/02* | (2006.01) | |
| *G06F 16/95* | (2019.01) | |
| *B62D 15/00* | (2006.01) | |
| *G01S 13/93* | (2006.01) | |
| *G06Q 30/02* | (2012.01) | |
| *G06F 16/29* | (2019.01) | |
| *G01C 21/34* | (2006.01) | |
| *G01C 21/36* | (2006.01) | |
| *B60R 11/04* | (2006.01) | |
| *B60S 1/62* | (2006.01) | |
| *G01S 7/40* | (2006.01) | |
| *G01S 7/497* | (2006.01) | |
| *G01S 13/86* | (2006.01) | |
| *G01S 17/89* | (2006.01) | |
| *G02B 27/00* | (2006.01) | |
| *B60W 30/09* | (2012.01) | |
| *B60W 50/00* | (2006.01) | |
| *G05D 1/00* | (2006.01) | |
| *G05D 1/02* | (2006.01) | |
| *A61B 5/01* | (2006.01) | |
| *A61B 5/024* | (2006.01) | |
| *A61B 5/08* | (2006.01) | |
| *A61B 5/16* | (2006.01) | |
| *A61B 5/18* | (2006.01) | |

(52) U.S. Cl.
CPC ............... *A61B 5/165* (2013.01); *A61B 5/18* (2013.01); *B60R 11/04* (2013.01); *B60S 1/62* (2013.01); *B60W 10/04* (2013.01); *B60W 10/18* (2013.01); *B60W 10/20* (2013.01); *B60W 30/09* (2013.01); *B60W 40/04* (2013.01); *B60W 40/08* (2013.01); *B60W 40/09* (2013.01); *B60W 40/105* (2013.01); *B60W 50/0097* (2013.01); *B60W 50/0098* (2013.01); *B60W 50/08* (2013.01); *B60W 50/082* (2013.01); *B62D 15/00* (2013.01); *B62D 15/0265* (2013.01); *G01C 21/3407* (2013.01); *G01C 21/3461* (2013.01); *G01C 21/3469* (2013.01); *G01C 21/3484* (2013.01); *G01C 21/3492* (2013.01); *G01C 21/3682* (2013.01); *G01C 21/3691* (2013.01); *G01C 21/3697* (2013.01); *G01S 7/4021* (2013.01); *G01S 7/497* (2013.01); *G01S 13/862* (2013.01); *G01S 13/865* (2013.01); *G01S 13/867* (2013.01); *G01S 13/87* (2013.01); *G01S 15/02* (2013.01); *G01S 17/89* (2013.01); *G02B 27/0006* (2013.01); *G05D 1/0061* (2013.01); *G05D 1/0088* (2013.01); *G05D 1/0212* (2013.01); *G05D 1/0214* (2013.01); *G05D 1/0221* (2013.01); *G05D 1/0276* (2013.01); *G06F 16/29* (2019.01); *G06F 16/95* (2019.01); *G06Q 30/0269* (2013.01); *G08G 1/161* (2013.01); *G08G 1/163* (2013.01); *G08G 1/164* (2013.01); *G08G 1/165* (2013.01); *G08G 1/166* (2013.01); *B60W 2040/0809* (2013.01); *B60W 2050/0004* (2013.01); *B60W 2050/0014* (2013.01); *B60W 2300/34* (2013.01); *B60W 2510/08* (2013.01); *B60W 2510/18* (2013.01); *B60W 2520/04* (2013.01); *B60W 2520/105* (2013.01); *B60W 2540/18* (2013.01); *B60W 2540/22* (2013.01); *B60W 2540/28* (2013.01); *B60W 2540/30* (2013.01); *B60W 2550/10* (2013.01); *B60W 2550/30* (2013.01); *B60W 2710/18* (2013.01); *B60W 2710/20* (2013.01); *B60W 2750/40* (2013.01); *B60W 2900/00* (2013.01); *G01S 2007/4043* (2013.01); *G01S 2007/4977* (2013.01); *G01S 2013/935* (2013.01); *G01S 2013/936* (2013.01); *G01S 2013/9325* (2013.01); *G01S 2013/9342* (2013.01); *G01S 2013/9346* (2013.01); *G01S 2013/9353* (2013.01); *G01S 2013/9357* (2013.01); *G01S 2013/9375* (2013.01); *G01S 2013/9378* (2013.01); *G01S 2013/9382* (2013.01); *G01S 2013/9385* (2013.01); *G01S 2013/9389* (2013.01); *G05D 2201/0212* (2013.01)

(56) References Cited

U.S. PATENT DOCUMENTS

| | | |
|---|---|---|
| 4,754,255 A | 6/1988 | Sanders et al. |
| 4,875,391 A | 10/1989 | Leising et al. |
| 5,136,498 A | 8/1992 | McLaughlin et al. |
| 5,204,817 A | 4/1993 | Yoshida |
| 5,363,306 A | 11/1994 | Kuwahara et al. |
| 5,508,689 A | 4/1996 | Rado et al. |
| 5,521,815 A | 5/1996 | Rose |
| 5,529,138 A | 6/1996 | Shaw et al. |
| 5,531,122 A | 7/1996 | Chatham et al. |
| 5,572,450 A | 11/1996 | Worthy |
| 5,610,821 A | 3/1997 | Gazis et al. |
| 5,648,769 A | 7/1997 | Sato et al. |
| 5,710,702 A | 1/1998 | Hayashi et al. |
| 5,794,164 A | 8/1998 | Beckert et al. |
| 5,797,134 A | 8/1998 | McMillan et al. |
| 5,812,067 A | 9/1998 | Bergholz et al. |
| 5,825,283 A | 10/1998 | Camhi |
| 5,838,251 A | 11/1998 | Brinkmeyer et al. |
| 5,847,661 A | 12/1998 | Ricci |
| 5,890,080 A | 3/1999 | Coverdill et al. |
| 5,928,294 A | 7/1999 | Zelinkovsky |
| 5,949,345 A | 9/1999 | Beckert et al. |
| 5,983,161 A | 11/1999 | Lemelson et al. |
| 5,986,575 A | 11/1999 | Jones et al. |
| 6,038,426 A | 3/2000 | Williams, Jr. |
| 6,081,756 A | 6/2000 | Mio et al. |
| D429,684 S | 8/2000 | Johnson |
| 6,128,003 A | 10/2000 | Smith et al. |
| 6,141,620 A | 10/2000 | Zyburt et al. |
| 6,148,261 A | 11/2000 | Obradovich et al. |
| 6,152,514 A | 11/2000 | McLellen |
| 6,157,321 A | 12/2000 | Ricci |
| 6,198,996 B1 | 3/2001 | Berstis |
| 6,199,001 B1 | 3/2001 | Ohta et al. |
| 6,202,008 B1 | 3/2001 | Beckert et al. |
| 6,252,544 B1 | 6/2001 | Hoffberg |
| 6,267,428 B1 | 7/2001 | Baldas et al. |
| 6,302,438 B1 | 10/2001 | Stopper, Jr. et al. |
| 6,310,542 B1 | 10/2001 | Gehlot |
| 6,317,058 B1 | 11/2001 | Lemelson et al. |
| 6,339,826 B2 | 1/2002 | Hayes, Jr. et al. |
| 6,356,838 B1 | 3/2002 | Paul |
| 6,388,579 B1 | 5/2002 | Adcox et al. |
| 6,480,224 B1 | 11/2002 | Brown |
| 6,502,022 B1 | 12/2002 | Chastain et al. |
| 6,519,519 B1 | 2/2003 | Stopczynski |
| 6,557,752 B1 | 5/2003 | Yacoob |
| 6,563,910 B2 | 5/2003 | Menard et al. |

(56) References Cited

U.S. PATENT DOCUMENTS

| | | |
|---|---|---|
| 6,587,739 B1 | 7/2003 | Abrams et al. |
| 6,598,227 B1 | 7/2003 | Berry et al. |
| 6,607,212 B1 | 8/2003 | Reimer et al. |
| 6,617,981 B2 | 9/2003 | Basinger |
| 6,662,077 B2 | 12/2003 | Haag |
| 6,675,081 B2 | 1/2004 | Shuman et al. |
| 6,678,747 B2 | 1/2004 | Goossen et al. |
| 6,681,176 B2 | 1/2004 | Funk et al. |
| 6,690,260 B1 | 2/2004 | Ashihara |
| 6,690,940 B1 | 2/2004 | Brown et al. |
| 6,724,920 B1 | 4/2004 | Berenz et al. |
| 6,754,580 B1 | 6/2004 | Ask et al. |
| 6,757,593 B2 | 6/2004 | Mori et al. |
| 6,762,684 B1 | 7/2004 | Camhi |
| 6,765,495 B1 | 7/2004 | Dunning et al. |
| 6,778,888 B2 | 8/2004 | Cataldo et al. |
| 6,782,240 B1 | 8/2004 | Tabe |
| 6,785,531 B2 | 8/2004 | Lepley et al. |
| 6,816,783 B2 | 11/2004 | Hashima et al. |
| 6,820,259 B1 | 11/2004 | Kawamata et al. |
| 6,944,533 B2 | 9/2005 | Obradovich et al. |
| 6,950,022 B2 | 9/2005 | Breed |
| 6,958,707 B1 | 10/2005 | Siegel |
| 6,992,580 B2 | 1/2006 | Kotzin et al. |
| 7,019,641 B1 | 3/2006 | Lakshmanan et al. |
| 7,020,544 B2 | 3/2006 | Shinada et al. |
| 7,021,691 B1 | 4/2006 | Schmidt et al. |
| 7,042,345 B2 | 5/2006 | Ellis |
| 7,047,129 B2 | 5/2006 | Uotani |
| 7,058,898 B2 | 6/2006 | McWalter et al. |
| 7,096,431 B2 | 8/2006 | Tambata et al. |
| 7,142,696 B1 | 11/2006 | Engelsberg et al. |
| 7,164,117 B2 | 1/2007 | Breed et al. |
| 7,187,947 B1 | 3/2007 | White et al. |
| 7,203,598 B1 | 4/2007 | Whitsell |
| 7,233,861 B2 | 6/2007 | Van Buer et al. |
| 7,239,960 B2 | 7/2007 | Yokota et al. |
| 7,277,454 B2 | 10/2007 | Mocek et al. |
| 7,284,769 B2 | 10/2007 | Breed |
| 7,289,645 B2 | 10/2007 | Yamamoto et al. |
| 7,295,921 B2 | 11/2007 | Spencer et al. |
| 7,313,547 B2 | 12/2007 | Mocek et al. |
| 7,333,012 B1 | 2/2008 | Nguyen |
| 7,343,148 B1 | 3/2008 | O'Neil |
| 7,386,376 B2 | 6/2008 | Basir et al. |
| 7,386,799 B1 | 6/2008 | Clanton et al. |
| 7,432,829 B2 | 10/2008 | Poltorak |
| 7,474,264 B2 | 1/2009 | Bolduc et al. |
| 7,493,140 B2 | 2/2009 | Michmerhuizen et al. |
| 7,526,539 B1 | 4/2009 | Hsu |
| 7,548,815 B2 | 6/2009 | Watkins et al. |
| 7,566,083 B2 | 7/2009 | Vitito |
| 7,606,660 B2 | 10/2009 | Diaz et al. |
| 7,606,867 B1 | 10/2009 | Singhal et al. |
| 7,643,913 B2 | 1/2010 | Taki et al. |
| 7,650,234 B2 | 1/2010 | Obradovich et al. |
| 7,671,764 B2 | 3/2010 | Uyeki et al. |
| 7,680,596 B2 | 3/2010 | Uyeki et al. |
| 7,683,771 B1 | 3/2010 | Loeb |
| 7,711,468 B1 | 5/2010 | Levy |
| 7,734,315 B2 | 6/2010 | Rathus et al. |
| 7,748,021 B2 | 6/2010 | Obradovich et al. |
| RE41,449 E | 7/2010 | Krahnstoever et al. |
| 7,791,499 B2 | 9/2010 | Mohan et al. |
| 7,796,190 B2 | 9/2010 | Basso et al. |
| 7,802,832 B2 | 9/2010 | Carnevali |
| 7,821,421 B2 | 10/2010 | Tamir et al. |
| 7,832,762 B2 | 11/2010 | Breed |
| 7,864,073 B2 | 1/2011 | Lee et al. |
| 7,872,591 B2 | 1/2011 | Kane et al. |
| 7,873,471 B2 | 1/2011 | Gieseke |
| 7,881,703 B2 | 2/2011 | Roundtree et al. |
| 7,891,004 B1 | 2/2011 | Gelvin et al. |
| 7,891,719 B2 | 2/2011 | Carnevali |
| 7,899,610 B2 | 3/2011 | McClellan |
| 7,966,678 B2 | 6/2011 | Ten Eyck et al. |
| 7,969,290 B2 | 6/2011 | Waeller et al. |
| 7,969,324 B2 | 6/2011 | Chevion et al. |
| 8,060,631 B2 | 11/2011 | Collart et al. |
| 8,064,925 B1 | 11/2011 | Sun et al. |
| 8,066,313 B2 | 11/2011 | Carnevali |
| 8,098,170 B1 | 1/2012 | Szczerba et al. |
| 8,113,564 B2 | 2/2012 | Carnevali |
| 8,131,419 B2 | 3/2012 | Ampunan et al. |
| 8,157,310 B2 | 4/2012 | Carnevali |
| 8,162,368 B2 | 4/2012 | Carnevali |
| 8,175,802 B2 | 5/2012 | Forstall et al. |
| 8,233,919 B2 | 7/2012 | Haag et al. |
| 8,245,609 B1 | 8/2012 | Greenwald et al. |
| 8,306,514 B1 | 11/2012 | Nunally |
| 8,334,847 B2 | 12/2012 | Tomkins |
| 8,346,233 B2 | 1/2013 | Aaron et al. |
| 8,346,432 B2 | 1/2013 | Van Wiemeersch et al. |
| 8,350,721 B2 | 1/2013 | Carr |
| 8,352,282 B2 | 1/2013 | Jensen et al. |
| 8,369,263 B2 | 2/2013 | Dowling et al. |
| 8,417,449 B1 | 4/2013 | Denise |
| 8,432,260 B2 | 4/2013 | Talty et al. |
| 8,442,389 B2 | 5/2013 | Kashima et al. |
| 8,442,758 B1 | 5/2013 | Rovik et al. |
| 8,467,965 B2 | 6/2013 | Chang |
| 8,497,842 B2 | 7/2013 | Tomkins et al. |
| 8,498,809 B2 | 7/2013 | Bill |
| 8,509,982 B2 | 8/2013 | Montemerlo et al. |
| 8,521,410 B2 | 8/2013 | Mizuno et al. |
| 8,527,143 B2 | 9/2013 | Tan |
| 8,527,146 B1 | 9/2013 | Jackson et al. |
| 8,532,574 B2 | 9/2013 | Kirsch |
| 8,543,330 B2 | 9/2013 | Taylor et al. |
| 8,547,340 B2 | 10/2013 | Sizelove et al. |
| 8,548,669 B2 | 10/2013 | Naylor |
| 8,559,183 B1 | 10/2013 | Davis |
| 8,577,600 B1 | 11/2013 | Pierfelice |
| 8,578,279 B2 | 11/2013 | Chen et al. |
| 8,583,292 B2 | 11/2013 | Preston et al. |
| 8,589,073 B2 | 11/2013 | Guha et al. |
| 8,600,611 B2 | 12/2013 | Seize |
| 8,613,385 B1 | 12/2013 | Hulet et al. |
| 8,621,645 B1 | 12/2013 | Spackman |
| 8,624,727 B2 | 1/2014 | Saigh et al. |
| 8,634,984 B2 | 1/2014 | Sumizawa |
| 8,644,165 B2 | 2/2014 | Saarimaki et al. |
| 8,660,735 B2 | 2/2014 | Tengler et al. |
| 8,671,068 B2 | 3/2014 | Harber et al. |
| 8,688,372 B2 | 4/2014 | Bhogal et al. |
| 8,705,527 B1 | 4/2014 | Addepalli et al. |
| 8,706,143 B1 | 4/2014 | Elias |
| 8,718,797 B1 | 5/2014 | Addepalli et al. |
| 8,725,311 B1 | 5/2014 | Breed |
| 8,730,033 B2 | 5/2014 | Yarnold et al. |
| 8,737,986 B2 | 5/2014 | Rhoads et al. |
| 8,761,673 B2 | 6/2014 | Sakata |
| 8,774,842 B2 | 7/2014 | Jones et al. |
| 8,779,947 B2 | 7/2014 | Tengler et al. |
| 8,782,262 B2 | 7/2014 | Collart et al. |
| 8,793,065 B2 | 7/2014 | Seltzer et al. |
| 8,798,918 B2 | 8/2014 | Onishi et al. |
| 8,805,110 B2 | 8/2014 | Rhoads et al. |
| 8,812,171 B2 | 8/2014 | Fillev et al. |
| 8,817,761 B2 | 8/2014 | Gruberman et al. |
| 8,825,031 B2 | 9/2014 | Aaron et al. |
| 8,825,277 B2 | 9/2014 | McClellan et al. |
| 8,825,382 B2 | 9/2014 | Liu |
| 8,826,261 B1 | 9/2014 | Anand AG et al. |
| 8,838,088 B1 | 9/2014 | Henn et al. |
| 8,862,317 B2 | 10/2014 | Shin et al. |
| 8,977,408 B1 | 3/2015 | Cazanas et al. |
| 9,043,016 B2 | 5/2015 | Filippov et al. |
| 9,229,905 B1 | 1/2016 | Penilla et al. |
| 2001/0010516 A1 | 8/2001 | Roh et al. |
| 2001/0015888 A1 | 8/2001 | Shaler et al. |
| 2002/0009978 A1 | 1/2002 | Dukach et al. |
| 2002/0023010 A1 | 2/2002 | Rittmaster et al. |
| 2002/0026278 A1 | 2/2002 | Feldman et al. |

(56) References Cited

U.S. PATENT DOCUMENTS

| | | |
|---|---|---|
| 2002/0045484 A1 | 4/2002 | Eck et al. |
| 2002/0065046 A1 | 5/2002 | Mankins et al. |
| 2002/0077985 A1 | 6/2002 | Kobata et al. |
| 2002/0095249 A1 | 7/2002 | Lang |
| 2002/0097145 A1 | 7/2002 | Tumey et al. |
| 2002/0103622 A1 | 8/2002 | Burge |
| 2002/0105968 A1 | 8/2002 | Pruzan et al. |
| 2002/0126876 A1 | 9/2002 | Paul et al. |
| 2002/0128774 A1 | 9/2002 | Takezaki et al. |
| 2002/0143461 A1 | 10/2002 | Burns et al. |
| 2002/0143643 A1 | 10/2002 | Catan |
| 2002/0152010 A1 | 10/2002 | Colmenarez et al. |
| 2002/0154217 A1 | 10/2002 | Ikeda |
| 2002/0169551 A1 | 11/2002 | Inoue et al. |
| 2002/0174021 A1 | 11/2002 | Chu et al. |
| 2003/0004624 A1 | 1/2003 | Wilson et al. |
| 2003/0007227 A1 | 1/2003 | Ogino |
| 2003/0046164 A1* | 3/2003 | Sato .............. G06Q 30/0265 705/14.66 |
| 2003/0055557 A1 | 3/2003 | Dutta et al. |
| 2003/0060937 A1 | 3/2003 | Shinada et al. |
| 2003/0065432 A1 | 4/2003 | Shuman et al. |
| 2003/0069870 A1 | 4/2003 | Ras et al. |
| 2003/0101451 A1 | 5/2003 | Bentolila et al. |
| 2003/0109972 A1 | 6/2003 | Tak |
| 2003/0125846 A1 | 7/2003 | Yu et al. |
| 2003/0132666 A1 | 7/2003 | Bond et al. |
| 2003/0149530 A1 | 8/2003 | Stopczynski |
| 2003/0158638 A1 | 8/2003 | Yakes et al. |
| 2003/0182435 A1 | 9/2003 | Redlich et al. |
| 2003/0202683 A1 | 10/2003 | Ma et al. |
| 2003/0204290 A1 | 10/2003 | Sadler et al. |
| 2003/0222134 A1* | 12/2003 | Boyd .............. G06Q 30/02 235/375 |
| 2003/0230443 A1 | 12/2003 | Cramer et al. |
| 2004/0017292 A1 | 1/2004 | Reese et al. |
| 2004/0024502 A1 | 2/2004 | Squires et al. |
| 2004/0036622 A1 | 2/2004 | Dukach et al. |
| 2004/0039500 A1 | 2/2004 | Amendola et al. |
| 2004/0039504 A1 | 2/2004 | Coffee et al. |
| 2004/0068364 A1 | 4/2004 | Zhao et al. |
| 2004/0070920 A1 | 4/2004 | Flueli |
| 2004/0093155 A1 | 5/2004 | Simonds et al. |
| 2004/0117494 A1 | 6/2004 | Mitchell et al. |
| 2004/0119589 A1* | 6/2004 | French .............. G06Q 10/025 340/539.11 |
| 2004/0128062 A1 | 7/2004 | Ogino et al. |
| 2004/0153356 A1 | 8/2004 | Lockwood et al. |
| 2004/0162019 A1 | 8/2004 | Horita et al. |
| 2004/0180653 A1 | 9/2004 | Royalty |
| 2004/0182574 A1 | 9/2004 | Adnan et al. |
| 2004/0193347 A1 | 9/2004 | Harumoto et al. |
| 2004/0203974 A1 | 10/2004 | Seibel |
| 2004/0204837 A1 | 10/2004 | Singleton |
| 2004/0209594 A1 | 10/2004 | Naboulsi |
| 2004/0217850 A1 | 11/2004 | Perttunen et al. |
| 2004/0225557 A1 | 11/2004 | Phelan et al. |
| 2004/0255123 A1 | 12/2004 | Noyama et al. |
| 2004/0257208 A1 | 12/2004 | Huang et al. |
| 2004/0260470 A1 | 12/2004 | Rast |
| 2005/0012599 A1 | 1/2005 | DeMatteo |
| 2005/0031100 A1 | 2/2005 | Iggulden et al. |
| 2005/0038598 A1 | 2/2005 | Oesterling et al. |
| 2005/0042999 A1 | 2/2005 | Rappaport |
| 2005/0065678 A1 | 3/2005 | Smith et al. |
| 2005/0065711 A1 | 3/2005 | Dahlgren et al. |
| 2005/0086051 A1 | 4/2005 | Brulle-Drews |
| 2005/0093717 A1 | 5/2005 | Lilja |
| 2005/0097541 A1 | 5/2005 | Holland |
| 2005/0114864 A1 | 5/2005 | Surace |
| 2005/0122235 A1 | 6/2005 | Teffer et al. |
| 2005/0124211 A1 | 6/2005 | Diessner et al. |
| 2005/0130744 A1 | 6/2005 | Eck et al. |
| 2005/0144156 A1 | 6/2005 | Barber |
| 2005/0149752 A1 | 7/2005 | Johnson et al. |
| 2005/0153760 A1 | 7/2005 | Varley |
| 2005/0159853 A1 | 7/2005 | Takahashi et al. |
| 2005/0159892 A1 | 7/2005 | Chung |
| 2005/0192727 A1 | 9/2005 | Shostak et al. |
| 2005/0197748 A1 | 9/2005 | Holst et al. |
| 2005/0197767 A1 | 9/2005 | Nortrup |
| 2005/0251324 A1 | 11/2005 | Wiener et al. |
| 2005/0261815 A1 | 11/2005 | Cowelchuk et al. |
| 2005/0278093 A1 | 12/2005 | Kameyama |
| 2005/0283284 A1 | 12/2005 | Grenier et al. |
| 2006/0015819 A1 | 1/2006 | Hawkins et al. |
| 2006/0036358 A1 | 2/2006 | Hale et al. |
| 2006/0044119 A1 | 3/2006 | Egelhaaf |
| 2006/0047386 A1 | 3/2006 | Kanevsky et al. |
| 2006/0058948 A1 | 3/2006 | Blass et al. |
| 2006/0059229 A1 | 3/2006 | Bain et al. |
| 2006/0125631 A1 | 6/2006 | Sharony |
| 2006/0130033 A1 | 6/2006 | Stoffels et al. |
| 2006/0142933 A1 | 6/2006 | Feng |
| 2006/0173841 A1 | 8/2006 | Bill |
| 2006/0175403 A1 | 8/2006 | McConnell et al. |
| 2006/0184319 A1 | 8/2006 | Seick et al. |
| 2006/0212909 A1 | 9/2006 | Girard et al. |
| 2006/0241836 A1 | 10/2006 | Kachouh et al. |
| 2006/0243056 A1 | 11/2006 | Sundermeyer et al. |
| 2006/0250272 A1 | 11/2006 | Puamau |
| 2006/0253307 A1 | 11/2006 | Warren et al. |
| 2006/0259210 A1 | 11/2006 | Tanaka et al. |
| 2006/0274829 A1 | 12/2006 | Siemens et al. |
| 2006/0282204 A1 | 12/2006 | Breed |
| 2006/0287807 A1 | 12/2006 | Teffer |
| 2006/0287865 A1 | 12/2006 | Cross et al. |
| 2006/0288382 A1 | 12/2006 | Vitito |
| 2006/0290516 A1 | 12/2006 | Muehlsteff et al. |
| 2007/0001831 A1 | 1/2007 | Raz et al. |
| 2007/0002032 A1 | 1/2007 | Powers et al. |
| 2007/0010942 A1 | 1/2007 | Bill |
| 2007/0015485 A1 | 1/2007 | DeBiasio et al. |
| 2007/0028370 A1 | 2/2007 | Seng |
| 2007/0032225 A1 | 2/2007 | Konicek et al. |
| 2007/0057781 A1 | 3/2007 | Breed |
| 2007/0061057 A1 | 3/2007 | Huang et al. |
| 2007/0067614 A1 | 3/2007 | Berry et al. |
| 2007/0069880 A1 | 3/2007 | Best et al. |
| 2007/0083298 A1 | 4/2007 | Pierce et al. |
| 2007/0088488 A1 | 4/2007 | Reeves et al. |
| 2007/0103328 A1 | 5/2007 | Lakshmanan et al. |
| 2007/0115101 A1 | 5/2007 | Creekbaum et al. |
| 2007/0118301 A1 | 5/2007 | Andarawis et al. |
| 2007/0120697 A1 | 5/2007 | Ayoub et al. |
| 2007/0135995 A1 | 6/2007 | Kikuchi et al. |
| 2007/0156317 A1 | 7/2007 | Breed |
| 2007/0182625 A1 | 8/2007 | Kerai et al. |
| 2007/0182816 A1 | 8/2007 | Fox |
| 2007/0185969 A1 | 8/2007 | Davis |
| 2007/0192486 A1 | 8/2007 | Wilson et al. |
| 2007/0194902 A1 | 8/2007 | Blanco et al. |
| 2007/0194944 A1 | 8/2007 | Galera et al. |
| 2007/0195997 A1 | 8/2007 | Paul et al. |
| 2007/0200663 A1 | 8/2007 | White et al. |
| 2007/0208860 A1 | 9/2007 | Zellner et al. |
| 2007/0213090 A1 | 9/2007 | Holmberg |
| 2007/0228826 A1 | 10/2007 | Jordan et al. |
| 2007/0233341 A1 | 10/2007 | Logsdon |
| 2007/0250228 A1 | 10/2007 | Reddy et al. |
| 2007/0257815 A1 | 11/2007 | Gunderson et al. |
| 2007/0276596 A1 | 11/2007 | Solomon et al. |
| 2007/0280505 A1 | 12/2007 | Breed |
| 2008/0005974 A1 | 1/2008 | Delgado Vazquez et al. |
| 2008/0023253 A1 | 1/2008 | Prost-Fin et al. |
| 2008/0027337 A1 | 1/2008 | Dugan et al. |
| 2008/0033635 A1 | 2/2008 | Obradovich et al. |
| 2008/0042824 A1 | 2/2008 | Kates |
| 2008/0051957 A1 | 2/2008 | Breed et al. |
| 2008/0052627 A1 | 2/2008 | Oguchi |
| 2008/0054072 A1* | 3/2008 | Katragadda .......... G08G 1/123 235/384 |
| 2008/0071465 A1 | 3/2008 | Chapman et al. |
| 2008/0082237 A1 | 4/2008 | Breed |

(56) References Cited

U.S. PATENT DOCUMENTS

| | | |
|---|---|---|
| 2008/0086455 A1 | 4/2008 | Meisels et al. |
| 2008/0090522 A1 | 4/2008 | Oyama |
| 2008/0104227 A1 | 5/2008 | Birnie et al. |
| 2008/0119994 A1 | 5/2008 | Kameyama |
| 2008/0129475 A1 | 6/2008 | Breed et al. |
| 2008/0143085 A1 | 6/2008 | Breed et al. |
| 2008/0147280 A1 | 6/2008 | Breed |
| 2008/0148374 A1 | 6/2008 | Spaur et al. |
| 2008/0154712 A1 | 6/2008 | Wellman |
| 2008/0154957 A1 | 6/2008 | Taylor et al. |
| 2008/0161986 A1 | 7/2008 | Breed |
| 2008/0164985 A1 | 7/2008 | Iketani et al. |
| 2008/0169940 A1 | 7/2008 | Lee et al. |
| 2008/0174451 A1 | 7/2008 | Harrington et al. |
| 2008/0212215 A1 | 9/2008 | Schofield et al. |
| 2008/0216067 A1 | 9/2008 | Villing |
| 2008/0228358 A1 | 9/2008 | Wang et al. |
| 2008/0234919 A1 | 9/2008 | Ritter et al. |
| 2008/0252487 A1 | 10/2008 | McClellan et al. |
| 2008/0253613 A1 | 10/2008 | Jones et al. |
| 2008/0255721 A1 | 10/2008 | Yamada |
| 2008/0255722 A1 | 10/2008 | McClellan et al. |
| 2008/0269958 A1 | 10/2008 | Filev et al. |
| 2008/0281508 A1 | 11/2008 | Fu |
| 2008/0300778 A1 | 12/2008 | Kuznetsov |
| 2008/0305780 A1 | 12/2008 | Williams et al. |
| 2008/0319602 A1 | 12/2008 | McClellan et al. |
| 2009/0006525 A1 | 1/2009 | Moore |
| 2009/0024419 A1 | 1/2009 | McClellan et al. |
| 2009/0037719 A1 | 2/2009 | Sakthikumar et al. |
| 2009/0040026 A1 | 2/2009 | Tanaka |
| 2009/0055178 A1 | 2/2009 | Coon |
| 2009/0082951 A1 | 3/2009 | Graessley |
| 2009/0099720 A1 | 4/2009 | Elgali |
| 2009/0112393 A1 | 4/2009 | Maten et al. |
| 2009/0112452 A1 | 4/2009 | Buck et al. |
| 2009/0119657 A1 | 5/2009 | Link, II |
| 2009/0125174 A1 | 5/2009 | Delean |
| 2009/0132294 A1 | 5/2009 | Haines |
| 2009/0138336 A1 | 5/2009 | Ashley et al. |
| 2009/0144622 A1 | 6/2009 | Evans et al. |
| 2009/0157312 A1 | 6/2009 | Black et al. |
| 2009/0158200 A1 | 6/2009 | Palahnuk et al. |
| 2009/0180668 A1 | 7/2009 | Jones et al. |
| 2009/0189373 A1 | 7/2009 | Schramm et al. |
| 2009/0189979 A1 | 7/2009 | Smyth |
| 2009/0193217 A1 | 7/2009 | Korecki et al. |
| 2009/0195370 A1 | 8/2009 | Huffman et al. |
| 2009/0210257 A1 | 8/2009 | Chalfant et al. |
| 2009/0216935 A1 | 8/2009 | Flick |
| 2009/0222200 A1 | 9/2009 | Link et al. |
| 2009/0224931 A1 | 9/2009 | Dietz et al. |
| 2009/0224942 A1 | 9/2009 | Goudy et al. |
| 2009/0234578 A1 | 9/2009 | Newby et al. |
| 2009/0241883 A1 | 10/2009 | Nagoshi et al. |
| 2009/0254446 A1 | 10/2009 | Chernyak |
| 2009/0264849 A1 | 10/2009 | La Croix |
| 2009/0275321 A1 | 11/2009 | Crowe |
| 2009/0278750 A1 | 11/2009 | Man et al. |
| 2009/0278915 A1 | 11/2009 | Kramer et al. |
| 2009/0279839 A1 | 11/2009 | Nakamura et al. |
| 2009/0284359 A1 | 11/2009 | Huang et al. |
| 2009/0287405 A1 | 11/2009 | Liu et al. |
| 2009/0299572 A1 | 12/2009 | Fujikawa et al. |
| 2009/0312998 A1 | 12/2009 | Berckmans et al. |
| 2009/0319181 A1 | 12/2009 | Khosravy et al. |
| 2010/0008053 A1 | 1/2010 | Osternack et al. |
| 2010/0023204 A1 | 1/2010 | Basir et al. |
| 2010/0035620 A1 | 2/2010 | Naden et al. |
| 2010/0036560 A1 | 2/2010 | Wright et al. |
| 2010/0042498 A1 | 2/2010 | Schalk |
| 2010/0052945 A1 | 3/2010 | Breed |
| 2010/0057337 A1 | 3/2010 | Fuchs |
| 2010/0066498 A1 | 3/2010 | Fenton |
| 2010/0069115 A1 | 3/2010 | Liu |
| 2010/0070338 A1 | 3/2010 | Siotia et al. |
| 2010/0077094 A1 | 3/2010 | Howarter et al. |
| 2010/0087987 A1 | 4/2010 | Huang et al. |
| 2010/0090817 A1 | 4/2010 | Yamaguchi et al. |
| 2010/0097178 A1 | 4/2010 | Pisz et al. |
| 2010/0097239 A1 | 4/2010 | Campbell et al. |
| 2010/0097458 A1 | 4/2010 | Zhang et al. |
| 2010/0106344 A1 | 4/2010 | Edwards et al. |
| 2010/0106418 A1 | 4/2010 | Kindo et al. |
| 2010/0118025 A1 | 5/2010 | Smith et al. |
| 2010/0121570 A1 | 5/2010 | Tokue et al. |
| 2010/0121645 A1 | 5/2010 | Seitz et al. |
| 2010/0125387 A1 | 5/2010 | Sehyun et al. |
| 2010/0125405 A1 | 5/2010 | Chae et al. |
| 2010/0125811 A1 | 5/2010 | Moore et al. |
| 2010/0127847 A1 | 5/2010 | Evans et al. |
| 2010/0131300 A1 | 5/2010 | Collopy et al. |
| 2010/0131642 A1* | 5/2010 | Chalikouras ........... G06Q 30/02 709/224 |
| 2010/0134958 A1 | 6/2010 | Disaverio et al. |
| 2010/0136944 A1 | 6/2010 | Taylor et al. |
| 2010/0137037 A1 | 6/2010 | Basir |
| 2010/0144284 A1 | 6/2010 | Chutorash et al. |
| 2010/0145700 A1 | 6/2010 | Kennewick et al. |
| 2010/0145987 A1 | 6/2010 | Harper et al. |
| 2010/0152976 A1 | 6/2010 | White et al. |
| 2010/0169432 A1 | 7/2010 | Santori et al. |
| 2010/0174474 A1 | 7/2010 | Nagase |
| 2010/0179712 A1 | 7/2010 | Pepitone et al. |
| 2010/0185341 A1 | 7/2010 | Wilson et al. |
| 2010/0188831 A1 | 7/2010 | Ortel |
| 2010/0197359 A1 | 8/2010 | Harris |
| 2010/0202346 A1 | 8/2010 | Sitzes et al. |
| 2010/0211259 A1 | 8/2010 | McClellan |
| 2010/0211282 A1 | 8/2010 | Nakata et al. |
| 2010/0211300 A1 | 8/2010 | Jaffe et al. |
| 2010/0211304 A1 | 8/2010 | Hwang et al. |
| 2010/0211441 A1 | 8/2010 | Sprigg et al. |
| 2010/0217458 A1 | 8/2010 | Schweiger et al. |
| 2010/0222939 A1 | 9/2010 | Namburu et al. |
| 2010/0228404 A1 | 9/2010 | Link et al. |
| 2010/0234071 A1 | 9/2010 | Shabtay et al. |
| 2010/0235042 A1 | 9/2010 | Ying |
| 2010/0235744 A1 | 9/2010 | Schultz |
| 2010/0235891 A1 | 9/2010 | Oglesbee et al. |
| 2010/0250071 A1 | 9/2010 | Pala et al. |
| 2010/0253493 A1 | 10/2010 | Szczerba et al. |
| 2010/0256836 A1 | 10/2010 | Mudalige |
| 2010/0259058 A1* | 10/2010 | Knighton ................ B60L 8/003 296/24.39 |
| 2010/0265104 A1 | 10/2010 | Zlojutro |
| 2010/0268426 A1 | 10/2010 | Pathak et al. |
| 2010/0274410 A1 | 10/2010 | Tsien et al. |
| 2010/0280751 A1 | 11/2010 | Breed |
| 2010/0287303 A1 | 11/2010 | Smith et al. |
| 2010/0289632 A1 | 11/2010 | Seder et al. |
| 2010/0289643 A1 | 11/2010 | Trundle et al. |
| 2010/0291427 A1 | 11/2010 | Zhou |
| 2010/0295676 A1 | 11/2010 | Khachaturov et al. |
| 2010/0304640 A1 | 12/2010 | Sofman et al. |
| 2010/0305807 A1 | 12/2010 | Basir et al. |
| 2010/0306080 A1 | 12/2010 | Trandal et al. |
| 2010/0306309 A1 | 12/2010 | Santori et al. |
| 2010/0306435 A1 | 12/2010 | Nigoghosian et al. |
| 2010/0315218 A1 | 12/2010 | Cades et al. |
| 2010/0321151 A1 | 12/2010 | Matsuura et al. |
| 2010/0325626 A1 | 12/2010 | Greschler et al. |
| 2010/0332130 A1 | 12/2010 | Shimizu et al. |
| 2011/0015853 A1 | 1/2011 | DeKock et al. |
| 2011/0018736 A1 | 1/2011 | Carr |
| 2011/0021213 A1 | 1/2011 | Carr |
| 2011/0021234 A1 | 1/2011 | Tibbits et al. |
| 2011/0028138 A1 | 2/2011 | Davies-Moore et al. |
| 2011/0035098 A1 | 2/2011 | Goto et al. |
| 2011/0035141 A1 | 2/2011 | Barker et al. |
| 2011/0040438 A1 | 2/2011 | Kluge et al. |
| 2011/0050589 A1 | 3/2011 | Yan et al. |
| 2011/0053506 A1 | 3/2011 | Lemke et al. |
| 2011/0077808 A1 | 3/2011 | Hyde et al. |

(56) References Cited

U.S. PATENT DOCUMENTS

| | | |
|---|---|---|
| 2011/0078024 A1 | 3/2011 | Messier et al. |
| 2011/0080282 A1 | 4/2011 | Kleve et al. |
| 2011/0082615 A1 | 4/2011 | Small et al. |
| 2011/0084824 A1 | 4/2011 | Tewari et al. |
| 2011/0090078 A1 | 4/2011 | Kim et al. |
| 2011/0092159 A1 | 4/2011 | Park et al. |
| 2011/0093154 A1 | 4/2011 | Moinzadeh et al. |
| 2011/0093158 A1 | 4/2011 | Theisen et al. |
| 2011/0093438 A1 | 4/2011 | Poulsen |
| 2011/0093846 A1 | 4/2011 | Moinzadeh et al. |
| 2011/0105097 A1 | 5/2011 | Tadayon et al. |
| 2011/0106375 A1 | 5/2011 | Sundaram et al. |
| 2011/0112717 A1 | 5/2011 | Resner |
| 2011/0112969 A1 | 5/2011 | Zaid et al. |
| 2011/0117933 A1 | 5/2011 | Andersson |
| 2011/0119344 A1 | 5/2011 | Eustis |
| 2011/0130915 A1 | 6/2011 | Wright et al. |
| 2011/0134749 A1 | 6/2011 | Speks et al. |
| 2011/0137520 A1 | 6/2011 | Rector et al. |
| 2011/0145331 A1 | 6/2011 | Christie et al. |
| 2011/0172873 A1 | 7/2011 | Szwabowski et al. |
| 2011/0175754 A1 | 7/2011 | Karpinsky |
| 2011/0183658 A1 | 7/2011 | Zellner |
| 2011/0187520 A1 | 8/2011 | Filev et al. |
| 2011/0193707 A1 | 8/2011 | Ngo |
| 2011/0193726 A1 | 8/2011 | Szwabowski et al. |
| 2011/0195699 A1 | 8/2011 | Tadayon et al. |
| 2011/0197187 A1 | 8/2011 | Roh |
| 2011/0205047 A1 | 8/2011 | Patel et al. |
| 2011/0209079 A1 | 8/2011 | Tarte et al. |
| 2011/0210867 A1 | 9/2011 | Benedikt |
| 2011/0212717 A1 | 9/2011 | Rhoads et al. |
| 2011/0221656 A1 | 9/2011 | Haddick et al. |
| 2011/0224865 A1 | 9/2011 | Gordon et al. |
| 2011/0224898 A1 | 9/2011 | Scofield et al. |
| 2011/0225527 A1 | 9/2011 | Law et al. |
| 2011/0227757 A1 | 9/2011 | Chen et al. |
| 2011/0231091 A1 | 9/2011 | Gourlay et al. |
| 2011/0234369 A1 | 9/2011 | Cai et al. |
| 2011/0245999 A1 | 10/2011 | Kordonowy |
| 2011/0246210 A1 | 10/2011 | Matsur |
| 2011/0247013 A1 | 10/2011 | Feller et al. |
| 2011/0251734 A1 | 10/2011 | Schepp et al. |
| 2011/0257973 A1 | 10/2011 | Chutorash et al. |
| 2011/0267204 A1 | 11/2011 | Chuang et al. |
| 2011/0267205 A1 | 11/2011 | McClellan et al. |
| 2011/0286676 A1 | 11/2011 | El Dokor |
| 2011/0291886 A1 | 12/2011 | Krieter |
| 2011/0291926 A1 | 12/2011 | Gokturk et al. |
| 2011/0298808 A1 | 12/2011 | Rovik |
| 2011/0301844 A1 | 12/2011 | Aono |
| 2011/0307354 A1 | 12/2011 | Erman et al. |
| 2011/0307570 A1 | 12/2011 | Speks |
| 2011/0309926 A1 | 12/2011 | Eikelenberg et al. |
| 2011/0309953 A1 | 12/2011 | Petite et al. |
| 2011/0313653 A1 | 12/2011 | Lindner |
| 2011/0320089 A1 | 12/2011 | Lewis |
| 2012/0006610 A1 | 1/2012 | Wallace et al. |
| 2012/0010807 A1 | 1/2012 | Zhou |
| 2012/0016581 A1 | 1/2012 | Mochizuki et al. |
| 2012/0029852 A1 | 2/2012 | Goff et al. |
| 2012/0030002 A1 | 2/2012 | Bous et al. |
| 2012/0030512 A1 | 2/2012 | Wadhwa et al. |
| 2012/0038489 A1 | 2/2012 | Goldshmidt |
| 2012/0046822 A1 | 2/2012 | Anderson |
| 2012/0047530 A1 | 2/2012 | Shkedi |
| 2012/0053793 A1 | 3/2012 | Sala et al. |
| 2012/0053888 A1 | 3/2012 | Stahlin et al. |
| 2012/0059789 A1 | 3/2012 | Sakai et al. |
| 2012/0065815 A1 | 3/2012 | Hess |
| 2012/0065834 A1 | 3/2012 | Senart |
| 2012/0068956 A1 | 3/2012 | Jira et al. |
| 2012/0071097 A1 | 3/2012 | Matsushita et al. |
| 2012/0072244 A1 | 3/2012 | Collins et al. |
| 2012/0074770 A1 | 3/2012 | Lee |
| 2012/0083960 A1 | 4/2012 | Zhu et al. |
| 2012/0083971 A1 | 4/2012 | Preston |
| 2012/0084773 A1 | 4/2012 | Lee et al. |
| 2012/0089299 A1 | 4/2012 | Breed |
| 2012/0092251 A1 | 4/2012 | Hashimoto et al. |
| 2012/0101876 A1 | 4/2012 | Truvey et al. |
| 2012/0101914 A1 | 4/2012 | Kumar et al. |
| 2012/0105613 A1 | 5/2012 | Weng et al. |
| 2012/0106114 A1 | 5/2012 | Caron et al. |
| 2012/0109446 A1 | 5/2012 | Yousefi et al. |
| 2012/0109451 A1 | 5/2012 | Tan |
| 2012/0110356 A1 | 5/2012 | Yousefi et al. |
| 2012/0113822 A1 | 5/2012 | Letner |
| 2012/0115446 A1 | 5/2012 | Guatama et al. |
| 2012/0116609 A1 | 5/2012 | Jung et al. |
| 2012/0116678 A1 | 5/2012 | Witmer |
| 2012/0116696 A1 | 5/2012 | Wank |
| 2012/0146766 A1 | 6/2012 | Geisler et al. |
| 2012/0146809 A1 | 6/2012 | Oh et al. |
| 2012/0149341 A1 | 6/2012 | Tadayon et al. |
| 2012/0150651 A1 | 6/2012 | Hoffberg et al. |
| 2012/0155636 A1 | 6/2012 | Muthaiah |
| 2012/0158436 A1 | 6/2012 | Bauer et al. |
| 2012/0173900 A1 | 7/2012 | Diab et al. |
| 2012/0173905 A1 | 7/2012 | Diab et al. |
| 2012/0179325 A1 | 7/2012 | Faenger |
| 2012/0179547 A1 | 7/2012 | Besore et al. |
| 2012/0188876 A1 | 7/2012 | Chow et al. |
| 2012/0197523 A1 | 8/2012 | Kirsch |
| 2012/0197669 A1 | 8/2012 | Kote et al. |
| 2012/0204166 A1 | 8/2012 | Ichihara |
| 2012/0210160 A1 | 8/2012 | Fuhrman |
| 2012/0215375 A1 | 8/2012 | Chang |
| 2012/0217928 A1 | 8/2012 | Kulidjian |
| 2012/0218125 A1 | 8/2012 | Demirdjian et al. |
| 2012/0226413 A1 | 9/2012 | Chen et al. |
| 2012/0238286 A1 | 9/2012 | Mallavarapu et al. |
| 2012/0239242 A1 | 9/2012 | Uehara |
| 2012/0242510 A1 | 9/2012 | Choi et al. |
| 2012/0254763 A1 | 10/2012 | Protopapas et al. |
| 2012/0254804 A1 | 10/2012 | Shema et al. |
| 2012/0259951 A1 | 10/2012 | Schalk et al. |
| 2012/0265359 A1 | 10/2012 | Das |
| 2012/0274459 A1 | 11/2012 | Jaisimha et al. |
| 2012/0274481 A1 | 11/2012 | Ginsberg et al. |
| 2012/0284080 A1 | 11/2012 | de Oliveira |
| 2012/0284292 A1 | 11/2012 | Rechsteiner et al. |
| 2012/0289217 A1 | 11/2012 | Reimer et al. |
| 2012/0289253 A1 | 11/2012 | Haag et al. |
| 2012/0296567 A1 | 11/2012 | Breed |
| 2012/0313771 A1 | 12/2012 | Wottlifff, III |
| 2012/0316720 A1 | 12/2012 | Hyde et al. |
| 2012/0317561 A1 | 12/2012 | Aslam et al. |
| 2012/0323413 A1 | 12/2012 | Kedar-Dongarkar et al. |
| 2012/0327231 A1 | 12/2012 | Cochran et al. |
| 2013/0005263 A1 | 1/2013 | Sakata |
| 2013/0005414 A1 | 1/2013 | Bindra et al. |
| 2013/0013157 A1 | 1/2013 | Kim et al. |
| 2013/0019252 A1 | 1/2013 | Haase et al. |
| 2013/0024060 A1 | 1/2013 | Sukkarie et al. |
| 2013/0029693 A1* | 1/2013 | Bradley, Jr. .......... H04W 4/029 455/456.3 |
| 2013/0030645 A1 | 1/2013 | Divine et al. |
| 2013/0030811 A1 | 1/2013 | Olleon et al. |
| 2013/0031540 A1 | 1/2013 | Throop et al. |
| 2013/0031541 A1 | 1/2013 | Wilks et al. |
| 2013/0035063 A1 | 2/2013 | Fisk et al. |
| 2013/0046624 A1 | 2/2013 | Calman |
| 2013/0050069 A1 | 2/2013 | Ota |
| 2013/0055096 A1 | 2/2013 | Kim et al. |
| 2013/0059607 A1 | 3/2013 | Herz et al. |
| 2013/0063336 A1 | 3/2013 | Sugimoto et al. |
| 2013/0066512 A1 | 3/2013 | Willard et al. |
| 2013/0067599 A1 | 3/2013 | Raje et al. |
| 2013/0075530 A1 | 3/2013 | Shander et al. |
| 2013/0079964 A1 | 3/2013 | Sukkarie et al. |
| 2013/0083805 A1 | 4/2013 | Lu et al. |
| 2013/0085787 A1 | 4/2013 | Gore et al. |
| 2013/0086164 A1 | 4/2013 | Wheeler et al. |

(56) References Cited

U.S. PATENT DOCUMENTS

| | | |
|---|---|---|
| 2013/0099915 A1 | 4/2013 | Prasad et al. |
| 2013/0103196 A1 | 4/2013 | Monceaux et al. |
| 2013/0116882 A1 | 5/2013 | Link et al. |
| 2013/0116915 A1 | 5/2013 | Ferreira et al. |
| 2013/0134730 A1 | 5/2013 | Ricci |
| 2013/0135118 A1 | 5/2013 | Ricci |
| 2013/0138591 A1 | 5/2013 | Ricci |
| 2013/0138714 A1 | 5/2013 | Ricci |
| 2013/0139140 A1 | 5/2013 | Rao et al. |
| 2013/0141247 A1 | 6/2013 | Ricci |
| 2013/0141252 A1 | 6/2013 | Ricci |
| 2013/0143495 A1 | 6/2013 | Ricci |
| 2013/0143546 A1 | 6/2013 | Ricci |
| 2013/0143601 A1 | 6/2013 | Ricci |
| 2013/0144459 A1 | 6/2013 | Ricci |
| 2013/0144460 A1 | 6/2013 | Ricci |
| 2013/0144461 A1 | 6/2013 | Ricci |
| 2013/0144462 A1 | 6/2013 | Ricci |
| 2013/0144463 A1 | 6/2013 | Ricci et al. |
| 2013/0144469 A1 | 6/2013 | Ricci |
| 2013/0144470 A1 | 6/2013 | Ricci |
| 2013/0144474 A1 | 6/2013 | Ricci |
| 2013/0144486 A1 | 6/2013 | Ricci |
| 2013/0144520 A1 | 6/2013 | Ricci |
| 2013/0144657 A1 | 6/2013 | Ricci |
| 2013/0145065 A1 | 6/2013 | Ricci |
| 2013/0145279 A1 | 6/2013 | Ricci |
| 2013/0145297 A1 | 6/2013 | Ricci et al. |
| 2013/0145360 A1 | 6/2013 | Ricci |
| 2013/0145401 A1 | 6/2013 | Ricci |
| 2013/0145482 A1 | 6/2013 | Ricci et al. |
| 2013/0147638 A1 | 6/2013 | Ricci |
| 2013/0151031 A1 | 6/2013 | Ricci |
| 2013/0151065 A1 | 6/2013 | Ricci |
| 2013/0151088 A1 | 6/2013 | Ricci |
| 2013/0151288 A1 | 6/2013 | Bowne et al. |
| 2013/0152003 A1 | 6/2013 | Ricci et al. |
| 2013/0154298 A1 | 6/2013 | Ricci |
| 2013/0157640 A1 | 6/2013 | Aycock |
| 2013/0157647 A1 | 6/2013 | Kolodziej |
| 2013/0158778 A1 | 6/2013 | Tengler et al. |
| 2013/0158821 A1 | 6/2013 | Ricci |
| 2013/0166096 A1 | 6/2013 | Jotanovic |
| 2013/0166097 A1 | 6/2013 | Ricci |
| 2013/0166098 A1 | 6/2013 | Lavie et al. |
| 2013/0166152 A1 | 6/2013 | Butterworth |
| 2013/0166208 A1 | 6/2013 | Forstall et al. |
| 2013/0167159 A1 | 6/2013 | Ricci et al. |
| 2013/0173531 A1 | 7/2013 | Rinearson et al. |
| 2013/0179689 A1 | 7/2013 | Matsumoto et al. |
| 2013/0190978 A1 | 7/2013 | Kato et al. |
| 2013/0194108 A1 | 8/2013 | Lapiotis et al. |
| 2013/0197796 A1 | 8/2013 | Obradovich et al. |
| 2013/0198031 A1 | 8/2013 | Mitchell et al. |
| 2013/0198737 A1 | 8/2013 | Ricci |
| 2013/0198802 A1 | 8/2013 | Ricci |
| 2013/0200991 A1 | 8/2013 | Ricci et al. |
| 2013/0203400 A1 | 8/2013 | Ricci |
| 2013/0204455 A1 | 8/2013 | Chia et al. |
| 2013/0204457 A1 | 8/2013 | King |
| 2013/0204466 A1 | 8/2013 | Ricci |
| 2013/0204484 A1 | 8/2013 | Ricci |
| 2013/0204493 A1 | 8/2013 | Ricci et al. |
| 2013/0204678 A1 | 8/2013 | Liu et al. |
| 2013/0204943 A1 | 8/2013 | Ricci |
| 2013/0205026 A1 | 8/2013 | Ricci |
| 2013/0205412 A1 | 8/2013 | Ricci |
| 2013/0207794 A1 | 8/2013 | Patel et al. |
| 2013/0212065 A1 | 8/2013 | Rahnama |
| 2013/0212659 A1 | 8/2013 | Maher et al. |
| 2013/0215116 A1 | 8/2013 | Siddique et al. |
| 2013/0218412 A1 | 8/2013 | Ricci |
| 2013/0218445 A1 | 8/2013 | Basir |
| 2013/0219039 A1 | 8/2013 | Ricci |
| 2013/0226365 A1 | 8/2013 | Brozovich |
| 2013/0226371 A1 | 8/2013 | Rovik et al. |
| 2013/0226392 A1 | 8/2013 | Schneider et al. |
| 2013/0226449 A1 | 8/2013 | Rovik et al. |
| 2013/0226622 A1 | 8/2013 | Adamson et al. |
| 2013/0227648 A1 | 8/2013 | Ricci |
| 2013/0231784 A1 | 9/2013 | Rovik et al. |
| 2013/0231800 A1 | 9/2013 | Ricci |
| 2013/0232142 A1 | 9/2013 | Nielsen et al. |
| 2013/0238165 A1 | 9/2013 | Garrett et al. |
| 2013/0241720 A1 | 9/2013 | Ricci et al. |
| 2013/0245882 A1 | 9/2013 | Ricci |
| 2013/0246181 A1 | 9/2013 | Lobsenz |
| 2013/0250933 A1 | 9/2013 | Yousefi et al. |
| 2013/0261871 A1 | 10/2013 | Hobbs et al. |
| 2013/0261966 A1 | 10/2013 | Wang et al. |
| 2013/0265178 A1 | 10/2013 | Tengler et al. |
| 2013/0274997 A1 | 10/2013 | Chien |
| 2013/0279111 A1 | 10/2013 | Lee |
| 2013/0279491 A1 | 10/2013 | Rubin et al. |
| 2013/0282238 A1 | 10/2013 | Ricci et al. |
| 2013/0282357 A1 | 10/2013 | Rubin et al. |
| 2013/0282946 A1 | 10/2013 | Ricci |
| 2013/0288606 A1 | 10/2013 | Kirsch |
| 2013/0293364 A1 | 11/2013 | Ricci et al. |
| 2013/0293452 A1 | 11/2013 | Ricci et al. |
| 2013/0293480 A1 | 11/2013 | Kritt et al. |
| 2013/0295901 A1 | 11/2013 | Abramson et al. |
| 2013/0295908 A1 | 11/2013 | Zeinstra et al. |
| 2013/0295913 A1 | 11/2013 | Matthews et al. |
| 2013/0300554 A1 | 11/2013 | Braden |
| 2013/0301584 A1 | 11/2013 | Addepalli et al. |
| 2013/0304371 A1 | 11/2013 | Kitatani et al. |
| 2013/0308265 A1 | 11/2013 | Arnouse |
| 2013/0309977 A1 | 11/2013 | Heines et al. |
| 2013/0311038 A1 | 11/2013 | Kim et al. |
| 2013/0325453 A1 | 12/2013 | Levien et al. |
| 2013/0325568 A1 | 12/2013 | Mangalvedkar et al. |
| 2013/0329372 A1 | 12/2013 | Wilkins |
| 2013/0332023 A1 | 12/2013 | Bertosa et al. |
| 2013/0338914 A1 | 12/2013 | Weiss |
| 2013/0339027 A1 | 12/2013 | Dokor et al. |
| 2013/0345929 A1 | 12/2013 | Bowden et al. |
| 2014/0028542 A1 | 1/2014 | Lovitt et al. |
| 2014/0032014 A1 | 1/2014 | DeBiasio et al. |
| 2014/0054957 A1 | 2/2014 | Bellis |
| 2014/0058672 A1 | 2/2014 | Wansley et al. |
| 2014/0058826 A1* | 2/2014 | Ogawa ............... G06Q 30/02 705/14.43 |
| 2014/0066014 A1 | 3/2014 | Nicholson et al. |
| 2014/0067201 A1 | 3/2014 | Visintainer et al. |
| 2014/0067564 A1 | 3/2014 | Yuan |
| 2014/0070917 A1 | 3/2014 | Protopapas |
| 2014/0081544 A1 | 3/2014 | Fry |
| 2014/0087760 A1* | 3/2014 | Bennett ............... H04W 4/21 455/456.3 |
| 2014/0088798 A1 | 3/2014 | Himmelstein |
| 2014/0095294 A1* | 4/2014 | Vick ............... G06Q 30/0266 705/14.43 |
| 2014/0096068 A1 | 4/2014 | Dewan et al. |
| 2014/0097955 A1 | 4/2014 | Lovitt et al. |
| 2014/0109075 A1 | 4/2014 | Hoffman et al. |
| 2014/0109080 A1 | 4/2014 | Ricci |
| 2014/0120829 A1 | 5/2014 | Bhamidipati et al. |
| 2014/0121862 A1 | 5/2014 | Zarrella et al. |
| 2014/0125802 A1 | 5/2014 | Beckert et al. |
| 2014/0143839 A1 | 5/2014 | Ricci |
| 2014/0164611 A1 | 6/2014 | Molettiere et al. |
| 2014/0168062 A1 | 6/2014 | Katz et al. |
| 2014/0168436 A1 | 6/2014 | Pedicino |
| 2014/0169621 A1 | 6/2014 | Burr |
| 2014/0171752 A1 | 6/2014 | Park et al. |
| 2014/0172727 A1 | 6/2014 | Abhyanker et al. |
| 2014/0188533 A1 | 7/2014 | Davidson |
| 2014/0188920 A1* | 7/2014 | Sharma ............... G06F 16/635 707/758 |
| 2014/0195272 A1 | 7/2014 | Sadiq et al. |
| 2014/0198216 A1 | 7/2014 | Zhai et al. |
| 2014/0200737 A1 | 7/2014 | Lortz et al. |
| 2014/0207328 A1 | 7/2014 | Wolf et al. |

(56) References Cited

U.S. PATENT DOCUMENTS

| | | |
|---|---|---|
| 2014/0220966 A1 | 8/2014 | Muetzel et al. |
| 2014/0222298 A1 | 8/2014 | Gurin |
| 2014/0222551 A1* | 8/2014 | Jain ................ G06Q 30/0246 705/14.42 |
| 2014/0223384 A1 | 8/2014 | Graumann |
| 2014/0240089 A1 | 8/2014 | Chang |
| 2014/0244078 A1 | 8/2014 | Downey et al. |
| 2014/0244111 A1 | 8/2014 | Gross et al. |
| 2014/0244156 A1 | 8/2014 | Magnusson et al. |
| 2014/0245277 A1 | 8/2014 | Petro et al. |
| 2014/0245278 A1 | 8/2014 | Zellen |
| 2014/0245284 A1 | 8/2014 | Alrabady et al. |
| 2014/0252091 A1 | 9/2014 | Morse et al. |
| 2014/0257627 A1 | 9/2014 | Hagan, Jr. |
| 2014/0267035 A1 | 9/2014 | Schalk et al. |
| 2014/0277936 A1 | 9/2014 | El Dokor et al. |
| 2014/0278070 A1 | 9/2014 | McGavran et al. |
| 2014/0278071 A1 | 9/2014 | San Filippo et al. |
| 2014/0281971 A1 | 9/2014 | Isbell, III et al. |
| 2014/0282161 A1 | 9/2014 | Cash |
| 2014/0282278 A1 | 9/2014 | Anderson et al. |
| 2014/0282470 A1 | 9/2014 | Buga et al. |
| 2014/0282931 A1 | 9/2014 | Protopapas |
| 2014/0292545 A1 | 10/2014 | Nemoto |
| 2014/0292665 A1 | 10/2014 | Lathrop et al. |
| 2014/0303899 A1 | 10/2014 | Fung |
| 2014/0306799 A1 | 10/2014 | Ricci |
| 2014/0306814 A1 | 10/2014 | Ricci |
| 2014/0306817 A1 | 10/2014 | Ricci |
| 2014/0306826 A1 | 10/2014 | Ricci |
| 2014/0306833 A1 | 10/2014 | Ricci |
| 2014/0306834 A1 | 10/2014 | Ricci |
| 2014/0306835 A1 | 10/2014 | Ricci |
| 2014/0307655 A1 | 10/2014 | Ricci |
| 2014/0307724 A1 | 10/2014 | Ricci |
| 2014/0308902 A1 | 10/2014 | Ricci |
| 2014/0309789 A1 | 10/2014 | Ricci |
| 2014/0309790 A1 | 10/2014 | Ricci |
| 2014/0309804 A1 | 10/2014 | Ricci |
| 2014/0309805 A1 | 10/2014 | Ricci |
| 2014/0309806 A1 | 10/2014 | Ricci |
| 2014/0309813 A1 | 10/2014 | Ricci |
| 2014/0309814 A1 | 10/2014 | Ricci et al. |
| 2014/0309815 A1 | 10/2014 | Ricci et al. |
| 2014/0309838 A1 | 10/2014 | Ricci |
| 2014/0309839 A1 | 10/2014 | Ricci et al. |
| 2014/0309847 A1 | 10/2014 | Ricci |
| 2014/0309849 A1 | 10/2014 | Ricci |
| 2014/0309852 A1 | 10/2014 | Ricci |
| 2014/0309853 A1 | 10/2014 | Ricci |
| 2014/0309862 A1 | 10/2014 | Ricci |
| 2014/0309863 A1 | 10/2014 | Ricci |
| 2014/0309864 A1 | 10/2014 | Ricci |
| 2014/0309865 A1 | 10/2014 | Ricci |
| 2014/0309866 A1 | 10/2014 | Ricci |
| 2014/0309867 A1 | 10/2014 | Ricci |
| 2014/0309868 A1 | 10/2014 | Ricci |
| 2014/0309869 A1 | 10/2014 | Ricci |
| 2014/0309870 A1 | 10/2014 | Ricci et al. |
| 2014/0309871 A1 | 10/2014 | Ricci |
| 2014/0309872 A1 | 10/2014 | Ricci |
| 2014/0309873 A1 | 10/2014 | Ricci |
| 2014/0309874 A1 | 10/2014 | Ricci |
| 2014/0309875 A1 | 10/2014 | Ricci |
| 2014/0309876 A1 | 10/2014 | Ricci |
| 2014/0309877 A1 | 10/2014 | Ricci |
| 2014/0309878 A1 | 10/2014 | Ricci |
| 2014/0309879 A1 | 10/2014 | Ricci |
| 2014/0309880 A1 | 10/2014 | Ricci |
| 2014/0309885 A1 | 10/2014 | Ricci |
| 2014/0309886 A1 | 10/2014 | Ricci |
| 2014/0309891 A1 | 10/2014 | Ricci |
| 2014/0309892 A1 | 10/2014 | Ricci |
| 2014/0309893 A1 | 10/2014 | Ricci |
| 2014/0309913 A1 | 10/2014 | Ricci et al. |
| 2014/0309919 A1 | 10/2014 | Ricci |
| 2014/0309920 A1 | 10/2014 | Ricci |
| 2014/0309921 A1 | 10/2014 | Ricci et al. |
| 2014/0309922 A1 | 10/2014 | Ricci |
| 2014/0309923 A1 | 10/2014 | Ricci |
| 2014/0309927 A1 | 10/2014 | Ricci |
| 2014/0309929 A1 | 10/2014 | Ricci |
| 2014/0309930 A1 | 10/2014 | Ricci |
| 2014/0309934 A1 | 10/2014 | Ricci |
| 2014/0309935 A1 | 10/2014 | Ricci |
| 2014/0309982 A1 | 10/2014 | Ricci |
| 2014/0310031 A1 | 10/2014 | Ricci |
| 2014/0310075 A1 | 10/2014 | Ricci |
| 2014/0310103 A1 | 10/2014 | Ricci |
| 2014/0310186 A1 | 10/2014 | Ricci |
| 2014/0310277 A1 | 10/2014 | Ricci |
| 2014/0310379 A1 | 10/2014 | Ricci et al. |
| 2014/0310594 A1 | 10/2014 | Ricci et al. |
| 2014/0310610 A1 | 10/2014 | Ricci |
| 2014/0310702 A1 | 10/2014 | Ricci et al. |
| 2014/0310739 A1 | 10/2014 | Ricci et al. |
| 2014/0310788 A1 | 10/2014 | Ricci |
| 2014/0322676 A1 | 10/2014 | Raman |
| 2014/0347207 A1 | 11/2014 | Zeng et al. |
| 2014/0347265 A1 | 11/2014 | Allen et al. |
| 2015/0007155 A1 | 1/2015 | Hoffman et al. |
| 2015/0012186 A1 | 1/2015 | Horseman |
| 2015/0032328 A1* | 1/2015 | Healey ................ B60Q 1/503 701/36 |
| 2015/0032366 A1 | 1/2015 | Man et al. |
| 2015/0032670 A1 | 1/2015 | Brazell |
| 2015/0057839 A1 | 2/2015 | Chang et al. |
| 2015/0061895 A1 | 3/2015 | Ricci |
| 2015/0081133 A1 | 3/2015 | Schulz |
| 2015/0081167 A1 | 3/2015 | Pisz et al. |
| 2015/0088423 A1 | 3/2015 | Tuukkanen |
| 2015/0088515 A1 | 3/2015 | Beaumont et al. |
| 2015/0106204 A1 | 4/2015 | Pudar |
| 2015/0116200 A1 | 4/2015 | Kurosawa et al. |
| 2015/0120135 A1* | 4/2015 | Lawrenson ......... B60W 50/085 701/36 |
| 2015/0158499 A1 | 6/2015 | Koravadi |
| 2015/0178034 A1 | 6/2015 | Penilla et al. |
| 2015/0262239 A1 | 9/2015 | Goralnick |
| 2015/0332330 A1 | 11/2015 | Dawson et al. |
| 2016/0008985 A1 | 1/2016 | Kim et al. |
| 2016/0070527 A1 | 3/2016 | Ricci |
| 2016/0086391 A1 | 3/2016 | Ricci |
| 2016/0232565 A1 | 8/2016 | Goergen |
| 2016/0247221 A1 | 8/2016 | Blumberg et al. |
| 2016/0253710 A1* | 9/2016 | Publicover ............ H04W 4/21 705/14.66 |
| 2016/0269456 A1 | 9/2016 | Ricci |
| 2016/0269469 A1 | 9/2016 | Ricci |
| 2017/0057516 A1* | 3/2017 | Gordon ................ B60W 40/08 |
| 2017/0217445 A1* | 8/2017 | Tzirkel-Hancock ....................... B60W 50/08 |
| 2017/0349184 A1* | 12/2017 | Tzirkel-Hancock ....................... B60W 50/08 |
| 2018/0122024 A1* | 5/2018 | Carpenter ......... G06Q 30/0235 |
| 2018/0137487 A1* | 5/2018 | Wang ................ G06Q 20/14 |
| 2019/0012324 A1* | 1/2019 | Parameswaran ............................ G06F 16/90324 |

FOREIGN PATENT DOCUMENTS

| | | |
|---|---|---|
| CN | 101303878 | 11/2008 |
| CN | 102467827 | 5/2012 |
| EP | 1223567 | 7/2002 |
| EP | 1484729 | 12/2004 |
| EP | 2192015 | 6/2010 |
| JP | 2004-284450 | 10/2004 |
| KR | 2006-0128484 | 12/2006 |
| WO | WO 2007/126204 | 11/2007 |
| WO | WO 2012/102879 | 8/2012 |
| WO | WO 2013/074866 | 5/2013 |
| WO | WO 2013/074867 | 5/2013 |
| WO | WO 2013/074868 | 5/2013 |

(56) References Cited

FOREIGN PATENT DOCUMENTS

| | | |
|---|---|---|
| WO | WO 2013/074897 | 5/2013 |
| WO | WO 2013/074899 | 5/2013 |
| WO | WO 2013/074901 | 5/2013 |
| WO | WO 2013/074919 | 5/2013 |
| WO | WO 2013/074981 | 5/2013 |
| WO | WO 2013/074983 | 5/2013 |
| WO | WO 2013/075005 | 5/2013 |
| WO | WO 2013/181310 | 12/2013 |
| WO | WO 2014/014862 | 1/2014 |
| WO | WO 2014/143563 | 9/2014 |
| WO | WO 2014/158667 | 10/2014 |
| WO | WO 2014/158672 | 10/2014 |
| WO | WO 2014/158766 | 10/2014 |
| WO | WO 2014/172312 | 10/2014 |
| WO | WO 2014/172313 | 10/2014 |
| WO | WO 2014/172316 | 10/2014 |
| WO | WO 2014/172320 | 10/2014 |
| WO | WO 2014/172322 | 10/2014 |
| WO | WO 2014/172323 | 10/2014 |
| WO | WO 2014/172327 | 10/2014 |
| WO | WO 2016/145073 | 9/2016 |
| WO | WO 2016/145100 | 9/2016 |

OTHER PUBLICATIONS

"Automatic vehicle location," Wikipedia, The Free Encyclopedia, Apr. 21, 2016 version, available at https://en.wikipedia.org/w/index.php?title=Automatic_vehicle_location&oldid=716386212, 6 pages.
"Automotive navigation system," Wikipedia, The Free Encyclopedia, Dec. 10, 2016 version, available at https://en.wikipedia.org/w/index.php?title=Automotive_navigation_system&oldid=753968543, 5 pages.
"Global positioning system," Wikipedia, The Free Encyclopedia, Dec. 29, 2016 version, available at https://en.wikipedia.org/w/index.php?title=Global_Positioning_System&oldid=757286677, 16 pages.
"Guide to Build Better Predictive Models using Segmentation," Analytics Vidyha Guest Blog, Feb. 26, 2016, available at https://www.analyticsvidhya.com/blog/2016/02/guide-build-predictive-models-segmentation/, 13 pages.
"Map database management," Wikipedia, The Free Encyclopedia, Nov. 15, 2016 version, available at https://en.wikipedia.org/w/index.php?title=Map_database_management&oldid=749668002, 7 pages.
"Nexus 10 Guidebook for Android," Google Inc., © 2012, Edition 1.2, 166 pages.
"Predictive analytics," Wikipedia, The Free Encyclopedia, Dec. 19, 2016 version, available at https://en.wikipedia.org/w/index.php?title=Predictive_analytics&oldid=755669107, 18 pages.
"Self-Driving: Self-Driving Autonomous Cars," available at http://www.automotivetechnologies.com/autonomous-self-driving-cars, accessed Dec. 2016, 9 pages.
Amor-Segan et al., "Towards the Self Healing Vehicle," Automotive Electronics, Jun. 2007, 2007 3rd Institution of Engineering and Technology Conference, 7 pages.
Bennett, "Meet Samsung's Version of Apple AirPlay," CNET.com, Oct. 10, 2012, 11 pages.
Cairnie et al., "Using Finger-Pointing to Operate Secondary Controls in Automobiles," Proceedings of the IEEE Intelligent Vehicles Symposium 2000, Oct. 3-5, 2000, 6 pages.
Clark, "How Self-Driving Cars Work: The Nuts and Bolts Behind Google's Autonomous Car Program," Feb. 21, 2015, available at http://www.makeuseof.com/tag/how-self-driving-cars-work-the-nuts-and-bolts-behind-googles-autonomous-car-program/, 9 pages.
Davies, "This NIO EP9 performance EV wants to be the Tesla of Supercars," SlashGear, 2016, retrieved from https//www.slashgear.com/nextev-nio-ep9-car-tesla-of-performance-evs-21464829, 6 pages.
Deaton et al., "How Driverless Cars Will Work," Jul. 1, 2008, HowStuffWorks.com. <http://auto.howstuffworks.com/under-the-hood/trends-innovations/driverless-car.htm> Sep. 18, 2017, 10 pages.
Dumbaugh, "Safe Streets, Livable Streets: A Positive Approach to urban Roadside Design," Ph.D. dissertation for School of Civil & Environ. Engr., Georgia Inst. of Technology, Dec. 2005, 235 pages.
Fei et al., "A QoS-aware Dynamic Bandwidth Allocation Algorithm for Relay Stations in IEEE 802.16j-based Vehicular Networks," Proceedings of the 2010 IEEE Global Telecommunications Conference, Dec. 10, 2010, 10 pages.
Ge et al., "Optimal Relay Selection in IEEE 802.16j Multihop Relay Vehicular Networks," IEEE Transactions on Vehicular Technology, 2010, vol. 59(5), pp. 2198-2206.
Guizzo, Erico, "How Google's Self-Driving Car Works," Oct. 18, 2011, available at https://spectrum.ieee.org/automaton/robotics/artificial-intelligence/how-google-self-driving-car-works, 5 pages.
Heer et al., "ALPHA: An Adaptive and Lightweight Protocol for Hop-by-hop Authentication," Proceedings of CoNEXT 2008, Dec. 2008, pp. 1-12.
Jahnich et al., "Towards a Middleware Approach for a Self-Configurable Automotive Embedded System," International Federation for Information Processing, 2008, pp. 55-65.
Kautonen, "NextEV unveils the NIO EP9 electric supercar in London," Autoblog, 2016, retrieved from http://www.autoblog.com/2016/11/21/nextev-unveiles-the-nio-ep9-electric-supercar-in-london/, 3 pages.
Pentland et al., "Modeling and Prediction of Human Behavior," Neural Computation, 1999, vol. 11, pp. 229-242.
Persson "Adaptive Middleware for Self-Configurable Embedded Real-Time Systems," KTH Industrial Engineering and Management, 2009, pp. iii-71 and references.
Raychaudhuri et al., "Emerging Wireless Technologies and the Future Mobile Internet," p. 48, Cambridge Press, 2011, 3 pages.
Stephens, Leah, "How Driverless Cars Work," Interesting Engineering, Apr. 28, 2016, available at https://interestingengineering.com/driverless-cars-work/, 7 pages.
Stoller, "Leader Election in Distributed Systems with Crash Failures," Indiana University, 1997, pp. 1-15.
Strunk et al., "The Elements of Style," 3d ed., Macmillan Publishing Co., 1979, 3 pages.
Suwatthikul, "Fault detection and diagnosis for in-vehicle networks," Intech, 2010, pp. 283-286 [retrieved from: www.intechopen.com/books/fault-detection-and-diagnosis-for-in-vehicle-networks].
Walter et al., "The smart car seat: personalized monitoring of vital signs in automotive applications." Personal and Ubiquitous Computing, Oct. 2011, vol. 15, No. 7, pp. 707-715.
White, "NextEV's NIO IP9 is an incredible four-wheel-rive electric hypercar," WIRED, 2016, retrieved from http://www.wired.co.uk/article/nextev-hypercar-nio-ep9, 6 pages.
Wolf et al., "Design, Implementation, and Evaluation of a Vehicular Hardware Security Module," ICISC'11 Proceedings of the 14th Int'l Conf. Information Security & Cryptology, Springer-Verlag Berlin, Heidelberg, 2011, pp. 302-318.
International Search Report and Written Opinion for PCT Application No. PCT/US2017/062709, dated Feb. 6, 2018, 25 pages.
International Preliminary Report on Patentability for PCT Application No. PCT/US2017/062709; dated May 31, 2019, 23 pages.

\* cited by examiner

METHOD AND SYSTEM FOR DATA OPTIMIZATION

CROSS REFERENCE TO RELATED APPLICATIONS

The present application claims the benefits of and priority, under 35 U.S.C. § 119(e), to U.S. Provisional Application Ser. No. 62/424,976, filed on Nov. 21, 2016, entitled "Next Generation Vehicle," the entire disclosure of which is hereby incorporated by reference, in its entirety, for all that it teaches and for all purposes.

FIELD

The present disclosure is generally directed to vehicle systems, in particular, toward electric and/or hybrid-electric vehicles.

BACKGROUND

In recent years, transportation methods have changed substantially. This change is due in part to a concern over the limited availability of natural resources, a proliferation in personal technology, and a societal shift to adopt more environmentally friendly transportation solutions. These considerations have encouraged the development of a number of new flexible-fuel vehicles, hybrid-electric vehicles, and electric vehicles.

While these vehicles appear to be new they are generally implemented as a number of traditional subsystems that are merely tied to an alternative power source. In fact, the design and construction of the vehicles is limited to standard frame sizes, shapes, materials, and transportation concepts. Among other things, these limitations fail to take advantage of the benefits of new technology, power sources, and support infrastructure. In particular, the implementation of an artificially intelligent vehicle has lagged far behind the development vehicle subsystems.

DETAILED DESCRIPTION

Embodiments of the present disclosure will be described in connection with a vehicle, and in some embodiments, an electric vehicle, rechargeable electric vehicle, and/or hybrid-electric vehicle and associated systems.

Embodiments can provide an intelligent vehicle that determines that the vehicle interior comprises multiple occupants; identifies the occupants; based on the driving behavior of the vehicle, creates a composite occupant profile associated with the group of plural occupants, the composite occupant profile comprising the identities of the plural occupants and group preferences for various vendor products or services; and, based on the composite occupant profile and received inputs from a user interface, an automatic vehicle location system, and a plurality of sensors in the vehicle, performs one or more actions, such as: (a) proposing one or more vendor products or services for the group of occupants; (b) publishing the vendor products or services selected by the group of occupants, via a social network, to associated or selected associates of the occupants in the group; and (c) presenting advertisement information from a vendor server associated with the proposed or selected vendor products or services to one or more of the occupants in the group.

The intelligent vehicle can anticipate the needs of individual occupants and groups of occupants and thereby reduce fewer operator distractions, provide a more pleasurable driving experience, enable more effective interaction between vendors and mobile customers, and publish automatically specified vehicle-collected information to a social network associated with an occupant. The ability to create and effectively use composite or group profiles can further reduce the time required for the group to agree upon a course of action or other option, reduce disagreements among vehicle occupants, and filter out unacceptable possible courses of action or options from those presented to the group.

Figure 1:
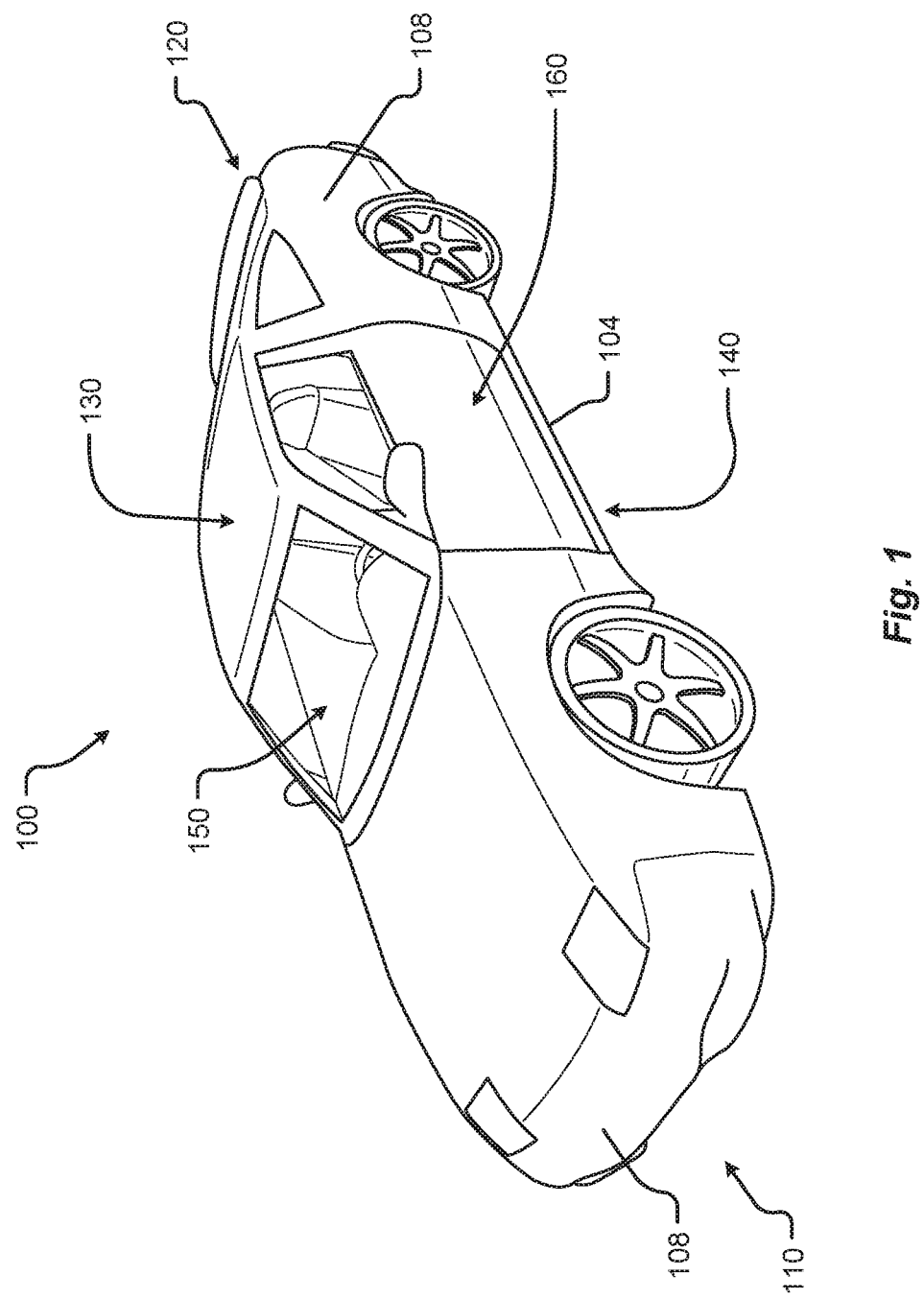
FIG. 1 shows a vehicle in accordance with embodiments of the present disclosure.

FIG. 1 shows a perspective view of a vehicle 100 in accordance with embodiments of the present disclosure. The electric vehicle 100 comprises a vehicle front 110, vehicle aft 120, vehicle roof 130, at least one vehicle side 160, a vehicle undercarriage 140, and a vehicle interior 150. In any event, the vehicle 100 may include a frame 104 and one or more body panels 108 mounted or affixed thereto. The vehicle 100 may include one or more interior components (e.g., components inside an interior space 150, or user space, of a vehicle 100, etc.), exterior components (e.g., components outside of the interior space 150, or user space, of a vehicle 100, etc.), drive systems, controls systems, structural components, etc.

Although shown in the form of a car, it should be appreciated that the vehicle 100 described herein may include any conveyance or model of a conveyance, where the conveyance was designed for the purpose of moving one or more tangible objects, such as people, animals, cargo, and the like. The term "vehicle" does not require that a conveyance moves or is capable of movement. Typical vehicles may include but are in no way limited to cars, trucks, motorcycles, busses, automobiles, trains, railed conveyances, boats, ships, marine conveyances, submarine conveyances, airplanes, space craft, flying machines, human-powered conveyances, and the like.

Figure 2:
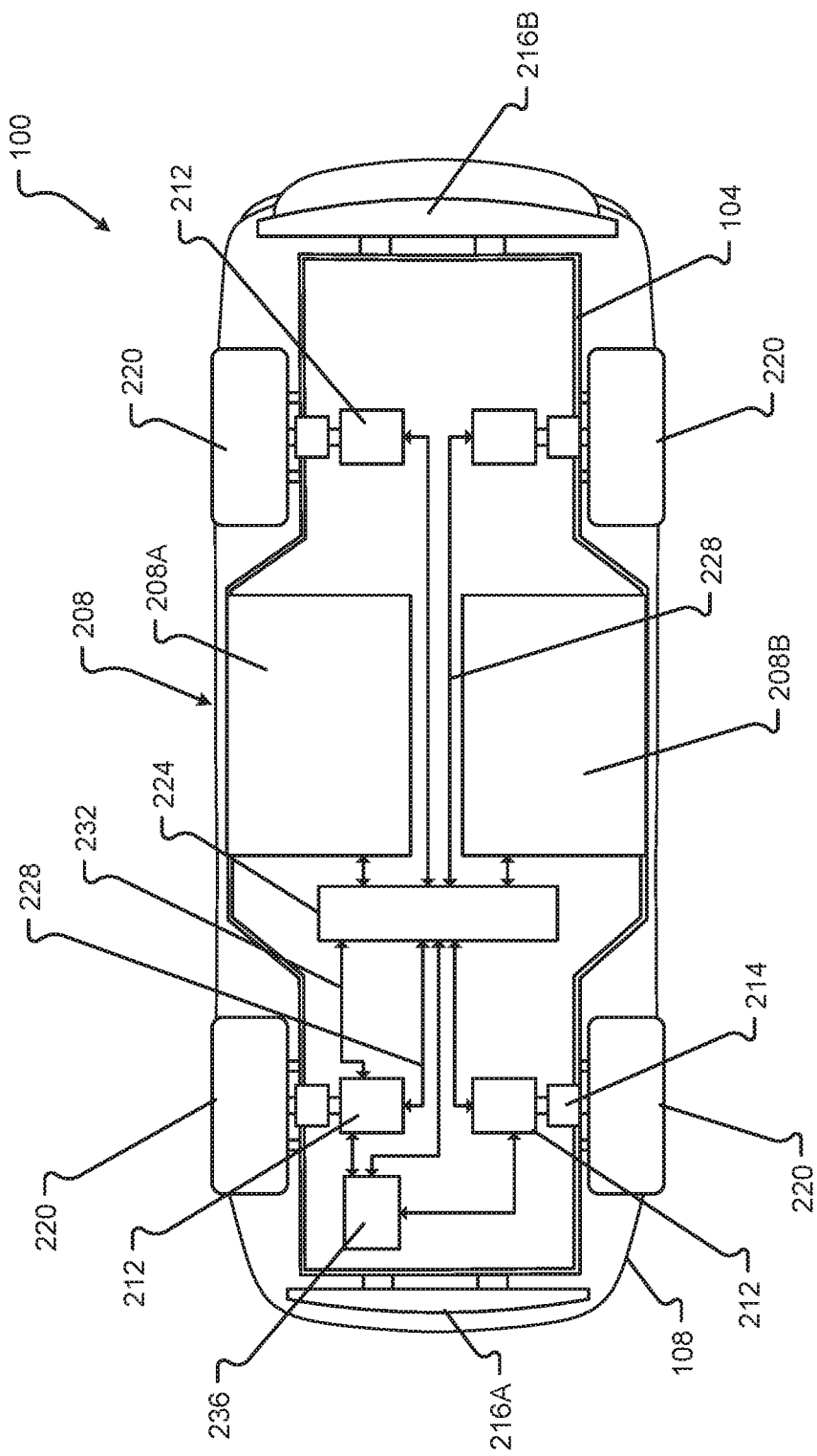
FIG. 2 shows a plan view of the vehicle in accordance with at least some embodiments of the present disclosure.

Referring now to FIG. 2, a plan view of an undercarriage vehicle 100 will be described in accordance with embodiments of the present disclosure. As provided above, the vehicle 100 may comprise a number of electrical and/or mechanical systems, subsystems, etc. The mechanical systems of the vehicle 100 can include structural, power, safety, and communications subsystems, to name a few. While each subsystem may be described separately, it should be appreciated that the components of a particular subsystem may be shared between one or more other subsystems of the vehicle 100.

The structural subsystem includes the frame 104 of the vehicle 100. The frame 104 may comprise one or more surfaces, connections, protrusions, cavities, mounting points, tabs, slots, or other features that are configured to receive other components that make up the vehicle 100. For example, the body panels 108, powertrain subsystem, controls systems, interior components, communications subsystem, and safety subsystem may interconnect with, or attach to, the frame 104 of the vehicle 100.

The frame 104 may attach or operatively engage one or more modular system and/or subsystems. Among other things, the frame can be attached to batteries, capacitors, power sources 208A, 208B, motors 212, engines, safety equipment, controllers, user interfaces, interiors exterior components, body panels 108, bumpers 216, sensors, etc., and/or combinations thereof.

The power system of the vehicle 100 may include the powertrain, power distribution system, accessory power system, and/or any other components that store power, provide power, convert power, and/or distribute power to one or more portions of the vehicle 100. The powertrain may include the one or more DC or AC electric motors 212 of the vehicle 100. The electric motors 212 are configured to convert electrical energy provided by a power source into mechanical energy to propel or otherwise provide a motive force for the vehicle 100.

In some embodiments, the vehicle 100 may include one or more drive wheels 220 that are driven by the one or more electric motors 212 and motor controllers 214. The powertrain may include one or more power transmission components, motor controllers 214, and/or power controllers that can provide a controlled output of power to one or more of the drive wheels 220 of the vehicle 100. The power transmission components, power controllers, or motor controllers 214 may be controlled by at least one other vehicle controller or computer system as described herein.

The power source 208 can include one or more energy storage systems comprising batteries or modules configured as a battery pack. The battery can be any type of battery for storing electrical energy, for example, a lithium ion battery, a lead acid battery, a nickel cadmium battery, etc. Further, the battery may include different types of power storage systems, such as, ionic fluids or other types of fuel cell systems. The energy storage systems may also include one or more high-capacity capacitors. The capacitors may be used for long-term or short-term storage of electrical energy.

The powertrain includes one or more power distribution systems configured to transmit power from the power source 208 to one or more electric motors 212 in the vehicle 100. The power distribution system may include electrical interconnections 228 and 232 in the form of cables, wires, traces, wireless power transmission systems, etc., and/or combinations thereof.

In some embodiments, the power distribution system may include an energy recovery system 236. This energy recovery system 236, or kinetic energy recovery system, may be configured to recover energy produced by the movement of a vehicle 100. The recovered energy may be stored as electrical and/or mechanical energy.

The vehicle 100 may include one or more safety systems. Vehicle safety systems can include a variety of mechanical and/or electrical components including, but in no way limited to, low impact or energy-absorbing bumpers 216A, 216B, crumple zones, reinforced body panels, reinforced frame components, impact bars, power source containment zones, safety glass, seatbelts, supplemental restraint systems, air bags, escape hatches, removable access panels, impact sensors, accelerometers, vision systems, radar systems, etc., and/or the like. In some embodiments, the one or more of the safety components may include a safety sensor or group of safety sensors associated with the one or more of the safety components. For example, a crumple zone may include one or more strain gages, impact sensors, pressure transducers, etc. These sensors may be configured to detect or determine whether a portion of the vehicle 100 has been subjected to a particular force, deformation, or other impact. Once detected, the information collected by the sensors may be transmitted or sent to one or more of a controller of the vehicle 100 (e.g., a safety controller, vehicle controller, etc.) or a communication device associated with the vehicle 100 (e.g., across a communication network, etc.).

Figure 3:
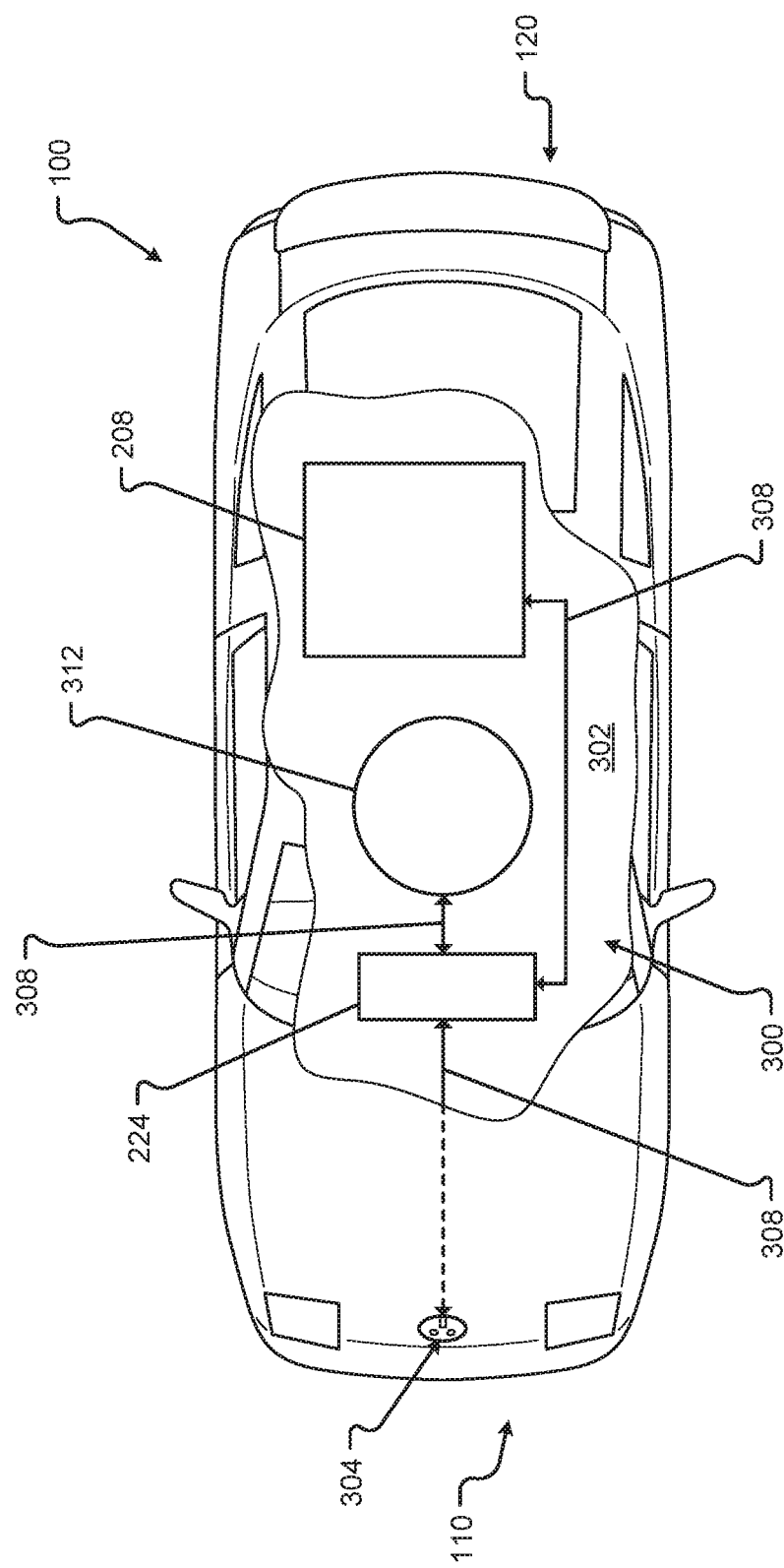
FIG. 3 shows a plan view of the vehicle in accordance with embodiments of the present disclosure

FIG. 3 shows a plan view of the vehicle 100 in accordance with embodiments of the present disclosure. In particular, FIG. 3 shows a broken section 302 of a charging system 300 for the vehicle 100. The charging system 300 may include a plug or receptacle 304 configured to receive power from an external power source (e.g., a source of power that is external to and/or separate from the vehicle 100, etc.). Power received at the plug/receptacle 304 may be transferred via at least one power transmission interconnection 308. Electrical energy in the form of charge can be transferred from the external power source to the charge controller 224. As provided above, the charge controller 224 may regulate the addition of charge to at least one power source 208 of the vehicle 100 (e.g., until the at least one power source 208 is full or at a capacity, etc.).

In addition to the mechanical components described herein, the vehicle 100 may include a number of user interface devices. The user interface devices receive and translate human input into a mechanical movement or electrical signal or stimulus. The human input may be one or more of motion (e.g., body movement, body part movement, in two-dimensional or three-dimensional space, etc.), voice, touch, and/or physical interaction with the components of the vehicle 100. In some embodiments, the human input may be configured to control one or more functions of the vehicle 100 and/or systems of the vehicle 100 described herein. User interfaces may include, but are in no way limited to, at least one graphical user interface of a display device, steering wheel or mechanism, transmission lever or button (e.g., including park, neutral, reverse, and/or drive positions, etc.), throttle control pedal or mechanism, brake control pedal or mechanism, power control switch, communications equipment, etc.

Figure 4:
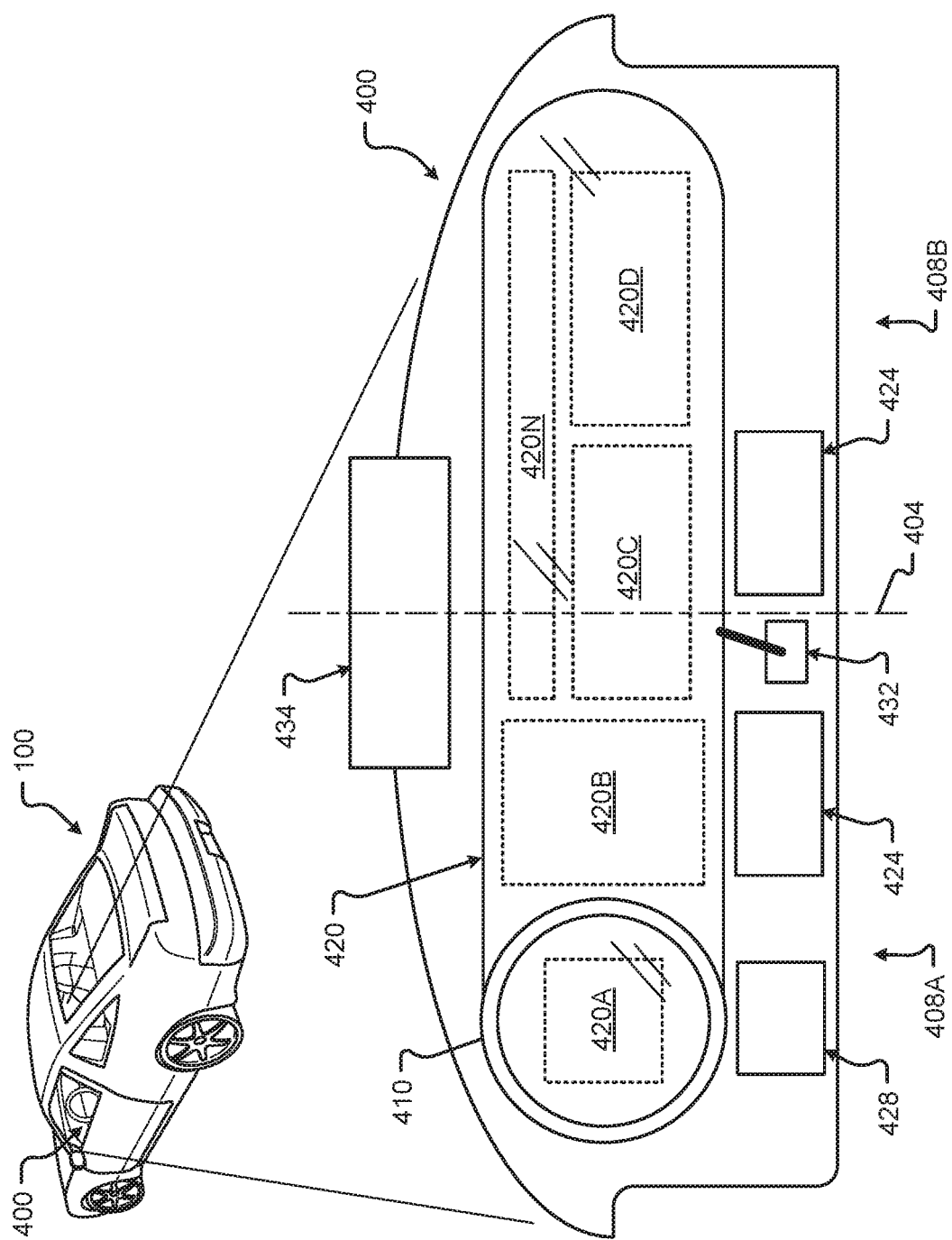
FIG. 4 shows an embodiment of the instrument panel of the vehicle according to one embodiment of the present disclosure.

FIG. 4 shows one embodiment of the instrument panel 400 of the vehicle 100. The instrument panel 400 of vehicle 100 comprises a steering wheel 410, a vehicle operational display 420 (e.g., configured to present and/or display driving data such as speed, measured air resistance, vehicle information, entertainment information, etc.), one or more auxiliary displays 424 (e.g., configured to present and/or display information segregated from the operational display 420, entertainment applications, movies, music, etc.), a heads-up display 434 (e.g., configured to display any information previously described including, but in no way limited to, guidance information such as route to destination, or obstacle warning information to warn of a potential collision, or some or all primary vehicle operational data such as speed, resistance, etc.), a power management display 428 (e.g., configured to display data corresponding to electric power levels of vehicle 100, reserve power, charging status, etc.), and an input device 432 (e.g., a controller, touchscreen, or other interface device configured to interface with one or more displays in the instrument panel or components of the vehicle 100. The input device 432 may be configured as a joystick, mouse, touchpad, tablet, 3D gesture capture device, etc.). In some embodiments, the input device 432 may be used to manually maneuver a portion of the vehicle 100 into a charging position (e.g., moving a charging plate to a desired separation distance, etc.).

While one or more of displays of instrument panel 400 may be touch-screen displays, it should be appreciated that the vehicle operational display may be a display incapable of receiving touch input. For instance, the operational display 420 that spans across an interior space centerline 404 and across both a first zone 408A and a second zone 408B may be isolated from receiving input from touch, especially from a passenger. In some cases, a display that provides vehicle operation or critical systems information and interface may be restricted from receiving touch input and/or be configured as a non-touch display. This type of configuration can prevent dangerous mistakes in providing touch input where such input may cause an accident or unwanted control.

In some embodiments, one or more displays of the instrument panel 400 may be mobile devices and/or applications residing on a mobile device such as a smart phone. Additionally or alternatively, any of the information described herein may be presented to one or more portions 420A-N of the operational display 420 or other display 424, 428, 434. In one embodiment, one or more displays of the instrument panel 400 may be physically separated or detached from the instrument panel 400. In some cases, a detachable display may remain tethered to the instrument panel.

The portions 420A-N of the operational display 420 may be dynamically reconfigured and/or resized to suit any display of information as described. Additionally or alternatively, the number of portions 420A-N used to visually present information via the operational display 420 may be dynamically increased or decreased as required, and are not limited to the configurations shown.

Figure 5:
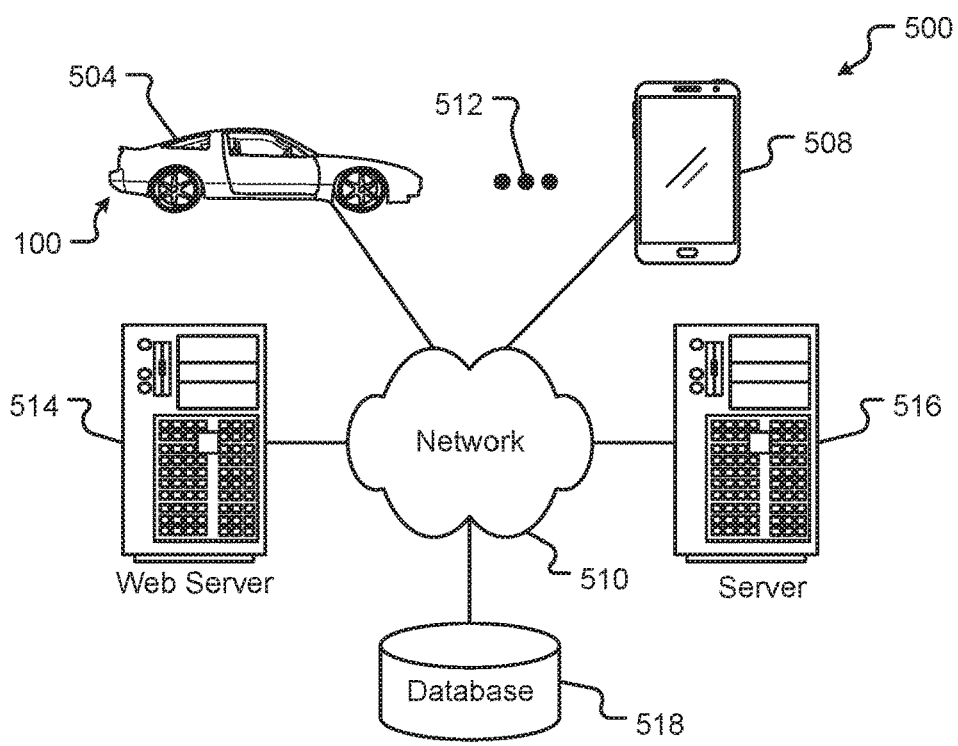
FIG. 5 is a block diagram of a computing environment associated with the embodiments presented herein.

FIG. 5 illustrates a block diagram of a computing environment 500 that may function as the servers, user computers, or other systems provided and described herein. The environment 500 includes one or more user computers, or computing devices, such as a vehicle computing device 504, a communication device 508, and/or more 512. The computing devices 504, 508, 512 may include general purpose personal computers (including, merely by way of example, personal computers, and/or laptop computers running various versions of Microsoft Corp.'s Windows® and/or Apple Corp.'s Macintosh® operating systems) and/or workstation computers running any of a variety of commercially-available UNIX® or UNIX-like operating systems. These computing devices 504, 508, 512 may also have any of a variety of applications, including for example, database client and/or server applications, and web browser applications. Alternatively, the computing devices 504, 508, 512 may be any other electronic device, such as a thin-client computer, Internet-enabled mobile telephone, computer wearable, and/ or personal digital assistant, capable of communicating via a network 510 and/or displaying and navigating web pages or other types of electronic documents. Although the exemplary computer environment 500 is shown with two computing devices, any number of user computers or computing devices may be supported.

Environment 500 further includes a network 510. The network 510 may can be any type of network familiar to those skilled in the art that can support data communications using any of a variety of commercially-available protocols, including without limitation SIP, TCP/IP, SNA, IPX, AppleTalk, and the like. Merely by way of example, the network 510 maybe a local area network ("LAN"), such as an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network (e.g., a network operating under any of the IEEE 802.9 suite of protocols, the Bluetooth® protocol known in the art, and/or any other wireless protocol); and/or any combination of these and/or other networks.

The system may also include one or more servers 514, 516. In this example, server 514 is shown as a web server and server 516 is shown as an application server. The web server 514, which may be used to process requests for web pages or other electronic documents from computing devices 504, 508, 512. The web server 514 can be running an operating system including any of those discussed above, as well as any commercially-available server operating systems. The web server 514 can also run a variety of server applications, including SIP (Session Initiation Protocol) servers, HTTP(s) servers, FTP servers, CGI servers, database servers, Java servers, and the like. In some instances, the web server 514 may publish operations available operations as one or more web services.

The environment 500 may also include one or more file and or/application servers 516, which can, in addition to an operating system, include one or more applications accessible by a client running on one or more of the computing devices 504, 508, 512. The server(s) 516 and/or 514 may be one or more general purpose computers capable of executing programs or scripts in response to the computing devices 504, 508, 512. As one example, the server 516, 514 may execute one or more web applications. The web application may be implemented as one or more scripts or programs written in any programming language, such as Java™, C, C#®, or C++, and/or any scripting language, such as Perl, Python, or TCL, as well as combinations of any programming/scripting languages. The application server(s) 516 may also include database servers, including without limitation those commercially available from Oracle®, Microsoft®, Sybase®, IBM® and the like, which can process requests from database clients running on a computing device 504, 508, 512.

The web pages created by the server 514 and/or 516 may be forwarded to a computing device 504, 508, 512 via a web (file) server 514, 516. Similarly, the web server 514 may be able to receive web page requests, web services invocations, and/or input data from a computing device 504, 508, 512 (e.g., a user computer, etc.) and can forward the web page requests and/or input data to the web (application) server 516. In further embodiments, the server 516 may function as a file server. Although for ease of description, FIG. 5 illustrates a separate web server 514 and file/application server 516, those skilled in the art will recognize that the functions described with respect to servers 514, 516 may be performed by a single server and/or a plurality of specialized servers, depending on implementation-specific needs and parameters. The computer systems 504, 508, 512, web (file) server 514 and/or web (application) server 516 may function as the system, devices, or components described in FIGS. 1-5.

The environment 500 may also include a database 518. The database 518 may reside in a variety of locations. By way of example, database 518 may reside on a storage medium local to (and/or resident in) one or more of the computers 504, 508, 512, 514, 516. Alternatively, it may be remote from any or all of the computers 504, 508, 512, 514, 516, and in communication (e.g., via the network 510) with one or more of these. The database 518 may reside in a storage-area network ("SAN") familiar to those skilled in the art. Similarly, any necessary files for performing the functions attributed to the computers 504, 508, 512, 514, 516 may be stored locally on the respective computer and/or remotely, as appropriate. The database 518 may be a relational database, such as Oracle 20i®, that is adapted to store, update, and retrieve data in response to SQL-formatted commands.

Figure 6:
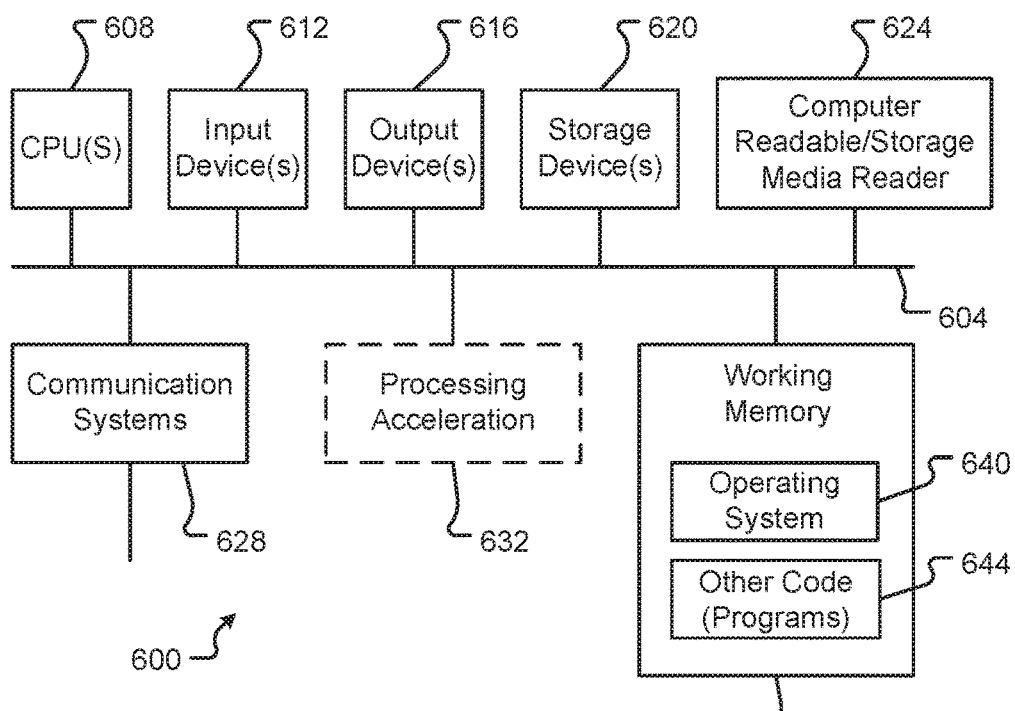
FIG. 6 is a block diagram of a computing device associated with one or more components described herein.

FIG. 6 illustrates one embodiment of a computer system 600 upon which the servers, user computers, computing devices, or other systems or components described above may be deployed or executed. The computer system 600 is shown comprising hardware elements that may be electrically coupled via a bus 604. The hardware elements may include one or more central processing units (CPUs) 608; one or more input devices 612 (e.g., a mouse, a keyboard, etc.); and one or more output devices 616 (e.g., a display device, a printer, etc.). The computer system 600 may also include one or more storage devices 620. By way of example, storage device(s) 620 may be disk drives, optical storage devices, solid-state storage devices such as a random access memory ("RAM") and/or a read-only memory ("ROM"), which can be programmable, flash-updateable and/or the like.

The computer system 600 may additionally include a computer-readable storage media reader 624; a communications system 628 (e.g., a modem, a network card (wireless or wired), an infra-red communication device, etc.); and working memory 636, which may include RAM and ROM devices as described above. The computer system 600 may also include a processing acceleration unit 632, which can include a DSP, a special-purpose processor, and/or the like.

The computer-readable storage media reader 624 can further be connected to a computer-readable storage medium, together (and, optionally, in combination with storage device(s) 620) comprehensively representing remote, local, fixed, and/or removable storage devices plus storage media for temporarily and/or more permanently containing computer-readable information. The communications system 628 may permit data to be exchanged with a network and/or any other computer described above with respect to the computer environments described herein. Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information.

The computer system 600 may also comprise software elements, shown as being currently located within a working memory 636, including an operating system 640 and/or other code 644. It should be appreciated that alternate embodiments of a computer system 600 may have numerous variations from that described above. For example, customized hardware might also be used and/or particular elements might be implemented in hardware, software (including portable software, such as applets), or both. Further, connection to other computing devices such as network input/output devices may be employed.

Examples of the processors 608 as described herein may include, but are not limited to, at least one of Qualcomm® Snapdragon® 800 and 801, Qualcomm® Snapdragon® 620 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, other industry-equivalent processors, and may perform computational functions using any known or future-developed standard, instruction set, libraries, and/or architecture.

Figure 7:
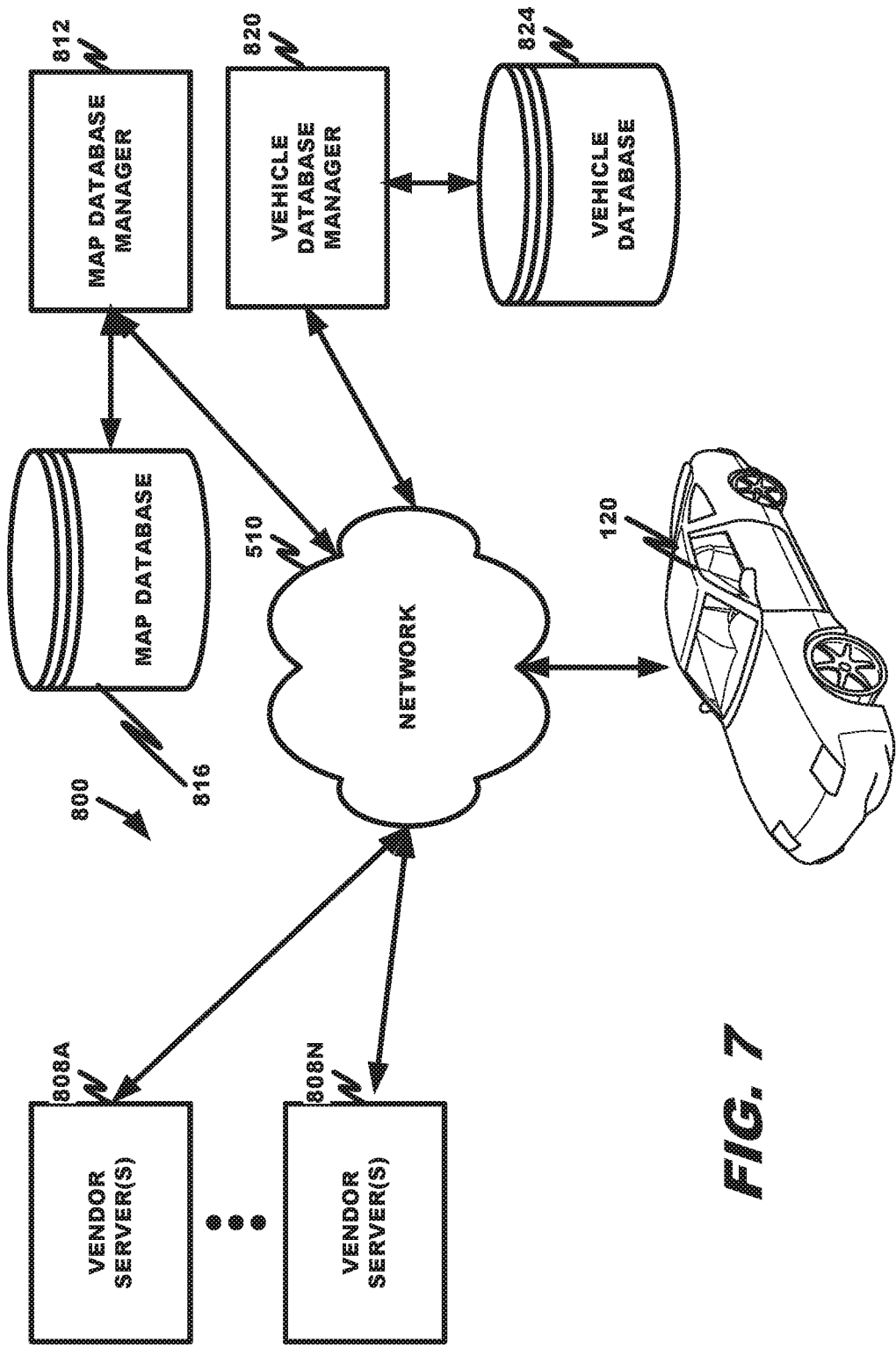
FIG. 7 is a block of a computing environment associated with the embodiments presented herein.

With reference to FIG. 7, the vehicle 120 is in wireless communication, via network 510, with one or more vendor server(s) 808A-N, a map database manager 812 and associated map database 816, and a vehicle database manager 820 and associated vehicle database 824.

FIG. 7 is a particular implementation of the computing environment of FIG. 5. The vendor server(s) 808A-N are each associated with a corresponding vendor location, such as a brick-and-mortar storefront or office building and communicate with the vehicle 120, map database manager 2012, and vehicle database manager 820 regarding information related to the respective vendor. For example, the vendor server 808 can provide to the vehicle 120 and/or map database manager 812 information related to the respective vendor and its product and/or service offerings, such as hours of operation, available product and/or service types, prices, brands, specifications, requirements, availabilities, advertising, and the like, sales specials and other price discounts and special offers and terms and conditions, referral percentages, fees, or payments for referring the vendor to an occupant of the vehicle 120, and other data element(s) and further data fields, such as geographical location of the respective vendor location, and the like.

The map database manager 812 and map database 816 interact with an automatic vehicle location system 908 (discussed below) in the vehicle 120 to provide navigation or map output to the vehicle occupants.

The map database manager 812 stores and recalls spatial map information from the map database 816.

The map database 816 contains plural maps. Maps are commonly stored as graphs, or two or three dimensional arrays of objects with attributes of location and category, where some common categories include parks, roads, cities, and the like. A map database commonly represents a road network along with associated features, with the road network corresponding to a selected road network model. Commonly, such a model comprises basic elements (nodes, links and areas) of the road network and properties of those elements (location coordinates, shape, addresses, road class, speed range, etc.). The basic elements are referred to as features and the properties as attributes. Other information associated with the road network can also be included, such as points of interest, waypoints, building shapes, and political boundaries. Geographic Data Files (GDF) is a standardized description of such a model. Each node within a map graph represents a point location of the surface of the Earth and can be represented by a pair of longitude (lon) and latitude (lat) coordinates. Each link can represent a stretch of road between two nodes, and be represented by a line segment (corresponding to a straight section of road) or a curve having a shape that is generally described by intermediate points (called shape points) along the link. However, curves can also be represented by a combination of centroid (point or node), with a radius, and polar coordinates to define the boundaries of the curve. Shape points can be represented by longitude and latitude coordinates as are nodes, but shape points generally do not serve the purpose of connecting links, as do nodes. Areas are generally two- or three-dimensional shapes that represent things like parks, cities, blocks and are defined by their boundaries (usually formed by a closed polygon).

Auxiliary data can be attached to the features and/or attributes. Various navigational functions, involving vendor information require data that is not considered to be part of a map database and is likely supplied by the vendor. This data (such as any of the data structures: information related to the respective vendor and its product and/or service offerings, such as hours of operation, available product and/or service types, prices, brands, specifications, requirements, availabilities, advertising, and the like, sales specials and other price discounts and special offers and terms and conditions, referral percentages, fees, or payments for referring the vendor to an occupant of the vehicle 120, and other data element(s) and further data fields, such as geographical location of the respective vendor location, and the like), should be cross-referenced with the entities and attributes of the main map database 816.

Since the auxiliary data is not necessarily compiled with the main map database some other means is generally needed to establish cross-referencing, which is referred to as attaching the auxiliary data. The common approaches are function-specific referencing tables and generic referencing.

Function-specific referencing tables provide a technique for attaching function-specific data to a map-data base produced by any participating vendor. Such a table can be collaboratively produced to support a specific function or class of functions involving location-based service, active-safety or advanced driver assistance. It will generally include a list of map elements of a specific type (e.g., links, intersections, point-of-interest locations, etc.) along with identifying attributes (e.g., street names, longitude/latitude coordinates, etc.). Additionally, each entry in the table can be assigned a unique identifier.

Generic referencing attaches data to any map database by discovering reference information through a form of map matching. The function-specific data items can be assigned to elements, such as points, links or areas, that likely only approximate the corresponding map elements in a specific map database. A search of the map database can be made for the best fit. To enhance the search process, neighboring elements can be appended to each given element to help ensure that the correct solution is found in each case. For example, if the map element is a link connecting two intersections, then one or both cross streets could be appended for the sake of the search thereby making an incorrect match unlikely.

The vehicle database manager 820 and vehicle database 824 interact with an automatic vehicle location system 908 (discussed below) in the vehicle 120 and vendor server(s) 808 to provide vehicle occupant information and vehicle location (such as determined by the automatic vehicle location system) to the vendor server(s) 808, provide received vendor information to the vehicle occupants, and effect payments by the corresponding vendor to the operator or owner of the vehicle database 824 for referrals. The owner of the vehicle database 824 is typically the vehicle manufacturer but can be any data management entity, such as a provider of satellite-based navigation information (e.g., Garmin™, Google™, Waze™, and the like), or an online network transportation company (such as Uber Technologies™ or Lyft™).

The vehicle database manager 812 stores and recalls vehicle and occupant information from the vehicle database 816.

The vehicle database 816 can be constructed according to any data model, whether conceptual, logical, or physical, such as a flat model, hierarchical model, network model, relational model, object-relational model, star schema, entity-relationship model, geographic model, generic model, semantic model, and the like. The data contained in the vehicle database 816 includes vehicle-related information (such as vehicle manufacturer, type, model, manufacture year, ownership, warranty coverage, serial number(s), current geographic location and occupant identifications, specifications, capabilities, currently sensed operational parameters for the vehicle, service history, and other information), occupant or potential occupant (whether operator or passenger) information (such as occupation, identities, age, sex, biometric information, authentication information, preferences, hobbies, and other interests, socioeconomic status, historic behavior patterns, profiles, transaction history with one or more vendors, nationality, ethnicity and race, language preferences (e.g., Spanish, English, Chinese, etc.), current occupant role (e.g., operator or passenger), Internet search history, social networking memberships and relationships, (e.g., friends), credit card and other financial information, electronic calendar information (e.g., Outlook™), medical information and history, and other information.

The vehicle database 816 can obtain occupant permissive access to the data collected by an occupant assistant in the vehicle by one or more techniques. In one technique, the purchaser of a vehicle is given a price discount in exchange for agreeing to enable the vehicle to collect certain types of data and provide the data to the vehicle database manager. In another technique, the occupant is given a financial incentive, such as price discounts on application offerings and other add-on services provided by an entity operating the vehicle database, in exchange for permitting the vehicle to collect and provide certain types of data to the vehicle database manager. In another technique, the occupant is provided with updates or application downloads in exchange for consenting to the vehicle collection and provision of certain types of data.

Figure 8:
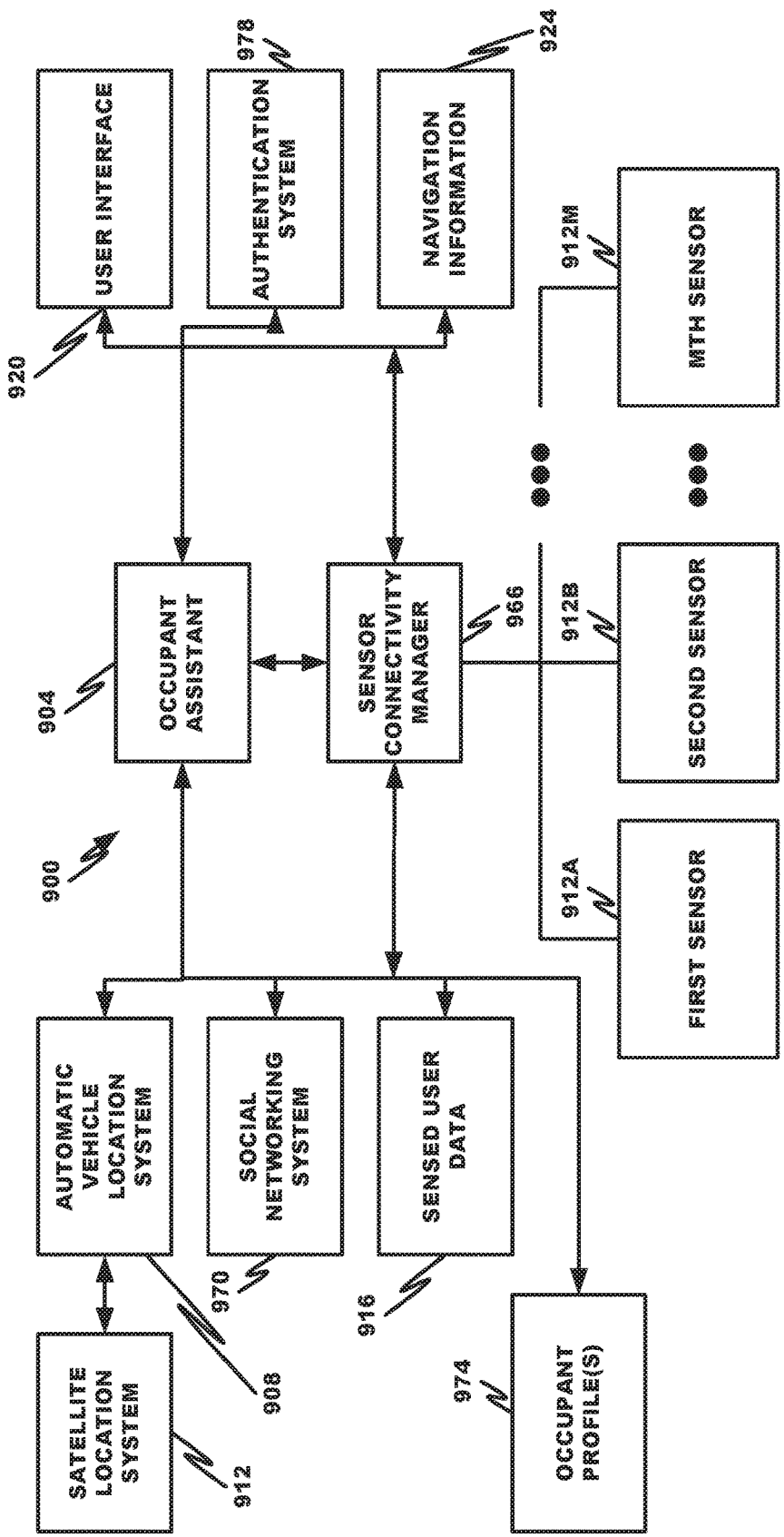
FIG. 8 is block diagram of a computational system in a vehicle and associated with one or more components described herein.

With reference to FIG. 8, an on board occupant interaction system 900 in the vehicle 120 is depicted. The interaction system 900 includes an occupant assistant 904 in communication with an automatic vehicle location system 908 and associated satellite location system 912, social networking system 970, sensed user data 916, occupant profile(s) 974, sensor connectivity manager 966 and associated first, second, . . . mth sensors 912A-M, user interface 920, authentication system 978, and navigation information 924.

The occupant assistant 904, based on received inputs from the automatic vehicle location system 908, social networking system 970, sensed user data 916, sensor connectivity manager 966, user interface 920, authentication system 978, and navigation information 924 received from the map database manager 812, can perform various functions including: proposing one or more destinations or waypoints (such as a restaurant, store, other vendor location, point of interest, etc.) in navigation information provided to an occupant, such as a driver, via the user interface 920; publishing occupant- or vehicle-related information, via a social network, to associated or selected associates of the occupant; collecting occupant- and vehicle-related information (including any of the information described above) and forwarding the collected information to a vendor server, map database manager 812, and/or vehicle database manager 820; and presenting advertisement information, such as web pages and hyperlinks, from a vendor server 808 or vehicle database manager 820 to an occupant. The occupant can select a recommended or suggested destination or waypoint, which is then updated by the vehicle map database manager 812 to direct the vehicle 120 to the waypoint or destination.

The automatic vehicle location system 908 is in communication with the satellite location system 912 (such as a Global Positioning System (or Navstar GPS) or GPS transmitter) to acquire current vehicle position coordinates, which position coordinates are then correlated by the map database manager 812 to a position on a road. Dead reckoning using distance data from one or more sensors 912 attached to the drive train, a gyroscope sensor 912 and/or an accelerometer sensor 912 can be used for greater reliability, as GPS signal loss and/or multipath can occur due to the map database manager 812, such as due to a cellular signal dead or low signal strength area or passage of the vehicle through a tunnel. As will be appreciated, a GPS satellite location system or GPS receiver, and when used for vehicle navigation commonly referred to simply as a GPS, is a device that is capable of receiving information from GPS satellites (not shown) and then to accurately calculate the GPS location system's geographical location. The GPS navigation device or GPS receiver can be on board the vehicle 120 on a portable computational or communication device of an occupant (such as a smart phone, tablet computer, personal navigation assistant, or laptop PC, As will be appreciated, any other satellite location or navigation system can be employed, such as GLOM SS, DeiDou Navigation Satellite System, Galileo, GAGAN, IRNSS, and the like.

The social networking system 970 maintains occupant social networking information, such as social networking service memberships or affiliations, associations with other social network members (e.g., friends), and member profiles, and posts or publishes content selected by the occupant assistant 904 to one or more social networking sites and/or friends selected by the occupant. For example, the social networking system 970 can post or publish selected sensed user data, such as occupant observations based on occupant driving behavior (e.g., a frequently visited location of the occupant), or vehicle data, such as vehicle geographical location.

The sensed user data 916 is user or occupant behavior and state information sensed by the on board computer in the vehicle 120, such as current or historical user driving behavior, historical user route, destination, and waypoint preferences, user identities, and the like. This information can be sensed by the first, second, . . . Mth sensor 912A-M. This information can be used by the occupant assistant 904 to develop an occupant profile 974.

The occupant profile 974 can include a variety of occupant information, including occupation, identity, age, sex, biometric information, authentication information, preferences, hobbies, and other interests, socioeconomic status, historic behavior patterns, profiles, visitation and/or transaction history with one or more vendors, nationality, ethnicity and race, language preferences (e.g., Spanish, English, Chinese, etc.), current occupant role (e.g., operator or passenger), occupant priority ranking (e.g., vehicle owner is given a higher ranking than a child occupant), Internet search history, social networking memberships and relationships, (e.g., friends), credit card and other financial information, electronic calendar information (e.g., Outlook™), medical information and history, and other information. The occupant profile 974 is normally attributed to the vehicle operator and the occupant preference values are populated and/or updated by the occupant assistant 904 or vehicle database manager 820 as the occupant operates the vehicle.

The first, second, . . . mth sensors 912a-m can include a camera to capture images captured of interior or exterior objects (such as occupants, roadways, roadside signals, and the like), a seat belt sensor to determine seat belt settings (e.g., closed or open), a seat weight sensor settings, a microphone to capture audio within the vehicle (such as occupant comments which are then input into a speech-tip-text engine to determine or identify one or more words spoken by an occupant), a wireless network node that receives unique identifiers of occupant portable computing devices (which identifiers can be associated with a corresponding occupant to identify the occupant), and the like. In some applications, a portable computing device of the occupant is employed as a sensor that tracks occupant location when he or she is absent from the vehicle, collects social networking service and site affiliations and member associations, Internet searches and browsing history, and other types and products of occupant behavior. The information is uploaded to the sensor connectivity manager 966 when the occupant returns to the vehicle. The sensor output provided, by the sensor connectivity manager 966, is then provided to the occupant assistant 904.

The user interface 920 receives user commands and other input, such as user selections, preferences, and settings that are used in configuring, determining, and selecting vehicle parameters, settings, or operations, such as navigation route selection, Internet search requests or browsing history, social networking service and site affiliations and member associations, and other types and products of occupant behavior. The user interface 920 can be one or more of vehicle instrument panel 400, vehicle operational display 420, heads-up display 434, and power management display 428. It can also be a portable computational or communication device of an occupant.

The authentication system 978 authenticates occupants using user selected credentials (e.g., password or personal identification number), a user computing device or keyfob emitted signal sequence or content (which sequence or content can be unique or substantially unique and therefore used to identify an associated user), and biometric physiological or behavioral information of the occupant, such as a fingerprint, palm vein pattern, facial characteristic, DNA sequence, palm print, hand geometry, iris characteristic, retina characteristic, odour/scent, occupant weight, and voice print or spectral characteristic. Behavioral biometric information includes seat settings, typing rhythm, and gait.

The navigation information 924 can take many forms depending on the configuration. When the navigation information 924 received by the vehicle from the automatic vehicle location system is provided, via network 510, to the map database manager 812, it can be the map or other navigation information provided by the map database manager 812 to the occupant, including possible routes and is periodically updated with selected route map information. When the navigation information is received by the automatic vehicle location system and used by the vehicle itself to configure, determine or select possible routes, it is map information from the map database 816 that is selected based on a request received by the map database manager 812 from the vehicle 120. The request can include the current vehicle location as determined by the automatic vehicle location system 908 and the locations of the user selected waypoints and destination.

A number of examples will now be used to explain the various operations of the occupant assistant 904.

In a first example, the occupant assistant 904, in response to a trigger such as time-of-day, vehicle location, a vehicle being parked, or other stimulus, determines a current location of the vehicle, retrieves a selected occupant or composite profile corresponding to a selected occupant of group of occupants currently in the vehicle, causes the map database manager 812 to search the map database 816 for specific information referenced in the selected occupant or composite profile, such as a restaurant, storefront, other vendor location, point of interest, and the like, within a defined spatial range of the vehicle, and, when a map feature matches the specific information, the occupant assistant 904 alerts one or more vehicle occupants, such as by updating a displayed navigation map or providing a message or prompt on the user interface or providing an audible voice message to the occupant(s) via a voice synthesizer.

In one variation of the first example, the occupant assistant 904 and/or vehicle database manager compares a need, specification, or requirement against a need, specification, or requirement of a vendor in determining whether or not to recommend or suggest the vendor to the selected occupant(s). For example, the occupant assistant 904 determines that the vehicle contains a family of four occupants (two adults and two children). The vehicle 904 directly or via the vehicle database manager, publishes this information to vendors within a selected spatial range of the current vehicle location (e.g., 2 miles). Each of the various vendors reviews its needs, specifications, requirements, or availabilities (e.g., it currently has an open table for a family of four) and responds with this information, possibly including a price discount or other incentive to the vehicle occupants, to select the respective vendor. Likewise, a vendor can review its needs, specifications, requirements, or availabilities and respond with a disincentive to the vehicle occupants to select its nearby vendor location. The response is received by the occupant assistant, which provides the response to one or more of the occupants or assigns a compliance score to each of the responses (based on occupant preferences and the attractiveness of the response to the needs, specifications or requirements of the occupant(s)), filters the various responses based on the assigned scores, and provides a subset of the responses to the one or more occupants. The occupant assistant 904 can, at the request of the one or more occupants, automatically make a reservation with the vendor (e.g., reserve the table).

In a second example, the occupant assistant 904, in response to a trigger such as time-of-day, vehicle location, a vehicle being parked, or other stimulus, determines a current location of the vehicle, retrieves a selected occupant or composite profile, causes the map database manager 812 to search the map database 816 for specific information referenced in the selected occupant or composite profile, such as a restaurant, storefront, other vendor location, point of interest, and the like, within a defined spatial range of the vehicle, and, when a map feature matches the specific information, publishes, as a recommendation, rating, or preference of the occupant or group of occupants, via a social networking service to the occupant friends or friends of each member of the group of occupants the located specific information. For example, the published information could be occupant X likes restaurant Y or occupant X is eating lunch at restaurant Y, and the like. Such a message could be customized for each occupant X in the occupant group and each friend Y of each occupant X.

In a third example, the occupant assistant 904 collects occupant- and vehicle-related information (including any of the information described above) and forwards the collected information to a vendor server, map database manager 812, and/or vehicle database manager 820. The vendor server can push advertisements to the occupant(s) via the user interface(s). The map database manager 812 or vehicle database manager 820 can use the collected information to update a profile of the occupant or composite profile of the occupant group, which is then provided to the occupant assistant for local storage as a profile 974.

In a fourth example, the occupant assistant 904 presents advertisement information, such as web pages and hyperlinks, from a vendor server 808 or vehicle database manager 820 to an occupant(s), monitors the occupant or occupant group behavior, such as a request to update the displayed navigation information to reflect a vendor location associated with the advertisement information or otherwise determines that the vehicle has traveled to the vendor location; and provides the visit to the vendor location to the vehicle database manager 820. The vehicle database manager 820 can determine from the vendor server associated with the visited vendor location that the occupant or a member of the occupant group has purchased goods or services. A referral fee, which can be a percentage of the transaction, a flat rate, or other basis, can be paid by the vendor to the entity operating the vehicle database manager. In some applications, the vehicle database manager uses information in the vehicle database to identify the vehicle occupant or a member of the occupant group as complying with stipulated criteria received from the vendor server (e.g., which criteria can be any of the occupant or vehicle information described above) and, when the occupant or occupant group is within a specified spatial range of a vendor location associated with the vendor server, alerts one or more of the occupant(s) to the vendor location or provides vendor generated advertisements to the vehicle for presentation to the occupant(s) and, in exchange receives a referral fee. Where the vendor location is in a mall, the occupant portable computing device can be used by the occupant assistant to track occupant or occupant group member location while the vehicle is parked and one or more of the occupants is absent.

When multiple occupants are in the vehicle, the occupant assistant 904 can blend profiles of the occupants to yield an aggregate or composite profile for use in any of the examples above. The composite profile recognizes that a given occupant's behavior when the occupant is alone is often different than the occupant's behavior when in a group. The composite profile for the group contains, in the occupant identity field, the identities of each of the occupants in the vehicle or occupant group. The role field, which defines the role of each individual participant in the behavior of the group on a group preference-by-preference basis or universally across all group preferences, contains a role value for each of the identified occupants. The role value indicates the degree of influence the corresponding occupant has over the behavior of the group. For example, a first occupant in the group has a first role value while a second occupant in the group has a different second role value, which means that the first and second occupants have different degrees of influence over the group behavior. The occupant having the superior role value has a greater weighting assigned to that occupant's field values in each of various group preference or predictive behavior fields. For a given field, the sum of all of the weighted values assigned to the group's occupant members is the aggregate value assigned to the field. By way of example, if a given field relates to preference for Italian food and first and second occupants are in the group, the value assigned to the field in the composite profile is (first occupant's preference value for Italian food)×(first occupant's role value)+(second occupant's preference value for Italian food)×(second occupant's role value)=group preference value for Italian food. When considering group preference for food type, the group food preference values for different food types are compared, with the field having the highest (or lowest depending on the configuration) group food preference value being the food type to be used in the restaurant search and recommendation. As will be appreciated, other approaches can be employed, such as assigning a restaurant preference field rather than food type preference.

When any field in the profiles of the various group members contains one or more conflicting values, a number of other different approaches can be used to resolve the conflict. In one approach, the most frequently occurring value for the field is given precedence for the entire carload of occupants regardless of the respective role ranking of each occupant, e.g., most passengers or occupants in the vehicle prefer Mexican food, a restaurant having outside seating, and/or romantic movies. In another approach, one occupant profile having a highest role ranking is given precedence over the profiles of the other occupants for the conflicting field. In another approach, the field is given multiple, different values, each of which can be the source of a stimulus or suggestion or recommendation. The occupants are then empowered to decide amongst themselves, what conflicting choice is to be selected. Other techniques can be used to resolve conflicting fields.

In yet another approach, the intelligent assistant 904 or vehicle database manager constructs a composite profile based on observations of vehicle behavior while the occupant group members are in a common vehicle. The observed vehicle behavior is attributed to the group rather than to the operator. As the vehicle is operated with the occupant group in the vehicle, the various group preference field values are populated and/or updated.

In yet another approach, the behavior of a given occupant or group of occupants is predicted using one or more dynamic models, such as predictive analytics (e.g., predictive models, descriptive models, and decision models), among others. The approaches used to conduct predictive analytics include regression techniques, linear regression models, discrete choice models, logistic regression, multinomial logistic regression, probit regression, time series models, survival or duration analysis, classification and regression trees, multivariate adaptive regression splines, machine learning techniques, neural networks, multilayer perception, radial basis functions, support vector machines, Naïve Bayes, k-nearest neighbors, and geospatial predictive modeling. One specific example is the use of plural Kalman filters sequenced by a Markov chain.

In yet another approach, the behavior of a given occupant or group of occupants is predicted using behavioral segmentation. Behavioral segmentation divides the occupants of multiple vehicles into groups or classes based on selected parameters of behavior, such as those set forth above. There are two broad set of methodologies for segmentation: namely objective (supervised) and lion-objective (unsupervised) segmentation methodologies. The most common techniques used for building an objective segmentation are CHAID and CRT. Each of these techniques attempts to maximize the difference among segments with regards to the stated objective or target for segmentation, which are the selected behavior parameters. CHAID uses a chi square statistic while CRT uses Gini impurity for the difference maximization. The most common techniques for building non-objective segmentation are cluster analysis and K nearest neighbor techniques. Each of these techniques uses a distance measure (e.g. Euclidian distance, Manhattan distance, or Mahalanobis distance). The distance measure maximizes the distance between the selected behavior parameters in the two segments.

In yet another approach, the behavior of a given occupant or group of occupants is predicted using occupant input on the selected parameters of behavior. The occupant input can be received by the user interface on board the vehicle.

When a given occupant is included in multiple composite profiles when he or she is in different occupant groups, the role and preference field values of the various composite profiles can be used to predict the given occupant's role value and preference field values of a different group of occupants containing different occupants besides the given occupant. This can be particularly true where the given occupant has a high or low role value consistently in the various composite values.

The operations of the various executable modules will now be discussed with reference to FIGS. 9-10.

Figure 9:
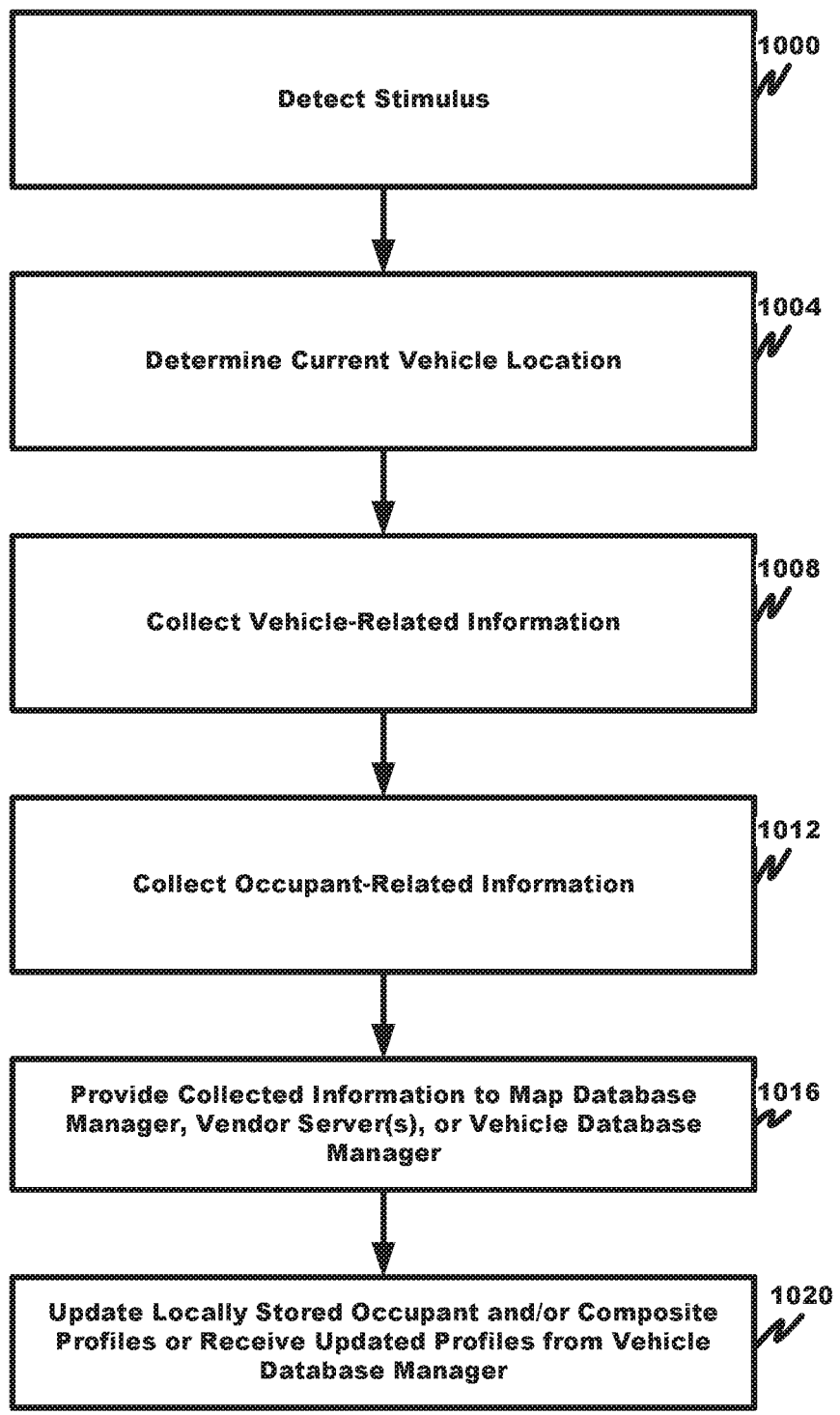
FIG. 9 is a flow chart associated with one or more embodiments presented herein.

With reference to FIG. 9, the occupant assistant 904, in step 1000, detects a stimulus, such as any set forth above, and commences execution of the instructions.

In step 1004, the occupant assistant 904 determines from the automatic vehicle location system 908 the current geographical location of the vehicle 120.

In step 1008, the occupant assistant 904 collects vehicle-related information from the sensor connectivity manager 966. This information comprises, in addition to the information set forth above, whether the vehicle is in park or in gear (e.g., motion), whether one or more occupants have left the vehicle (e.g. by sensing door openings or closings, by processing an image of the vehicle interior to detect an absent occupant, detecting a change of sensed weight by a seat weight sensor or change of safety belt setting (e.g., open or closed), and the like.

In step 1012, the occupant assistant 904 collects occupant-related information, such as the information set forth above. This includes, for example, the identities of the vehicle occupants, the roles of each identified occupant (e.g., driver or passenger), a current activity of each occupant (e.g., operating vehicle, operating portable computing device, interacting with an on board vehicle user interface, and the like), content provided to each identified occupant since the last data collection (e.g., Internet search or browsing session content, such as web pages), and the like.

In step 1016, the occupant assistant 904, depending on the embodiment, provides the collected information to the map database manager, vendor server(s), or vehicle database manager to update a set of occupant-related or vehicle-related data structures maintained thereby.

In step 1020, the occupant assistant 908 optionally updates locally stored occupant profiles 974 or receives updated occupant and composite profiles from the vehicle database manager.

Figure 10:
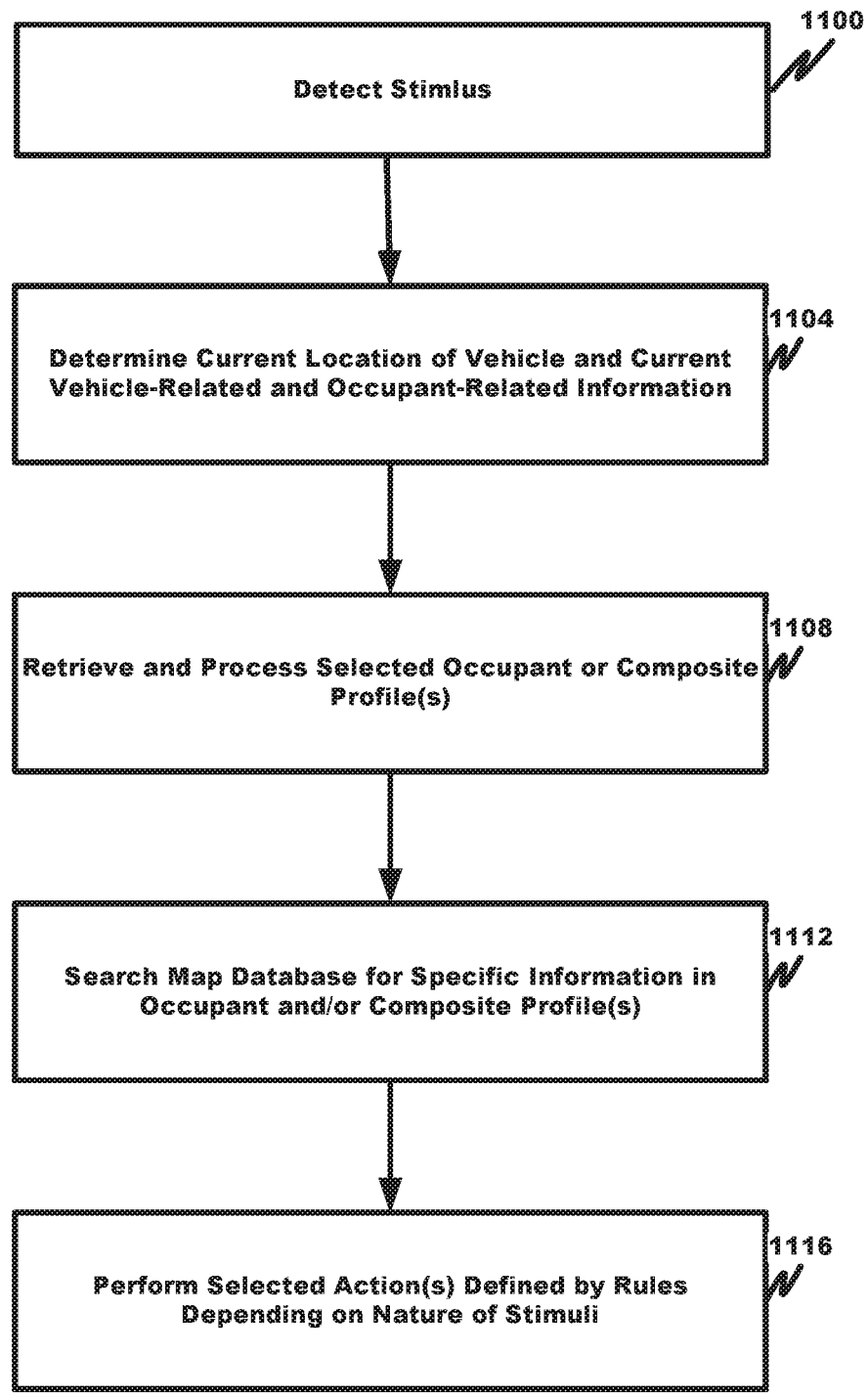
FIG. 10 is a flow chart associated with one or more embodiments presented herein.

With reference to FIG. 10, the occupant assistant 904, in step 1100, detects a stimulus, such as any set forth above and receipt of a request from a vendor server, map database manager, or vehicle database manager, and commences execution of the instructions.

In step 1104, the occupant assistant 904 determines from the automatic vehicle location system 908 the current geographical location of the vehicle 120 and, from sensed user data 916, the current vehicle-related and occupant-related information.

In step 1108, the occupant assistant 904 retrieves selected occupant or composite profile(s), typically for each occupant in the vehicle.

In step 1112, the occupant assistant 904 causes the map database manager to search the map database for specific information in the occupant or composite profile(s). The data structures searched can be auxiliary data embedded in the map information. The type of specific information to be searched depends on the nature of the stimulus. If the stimulus is detection of a habitual or predetermined time to consume breakfast, lunch, or dinner, the occupant assistant selects food preference or preferred restaurants fields. If the stimulus is receipt of a request from a vendor server or vehicle database manager for a request to provide potential advertisement information or recommendation or suggestion to visit a vendor, the fields selected relate to conditions set forth in the request defining preconditions for the potential advertisement or recommendation or suggestion (e.g., occupant age, sex, socioeconomic status, interaction history of occupant with the vendor, and the like).

In step 1116, the occupant assistant 904, depending on the nature of the stimuli and results of search, applies rules defining what, if any, actions are to be undertaken. Actions include, for example, proposing one or more destinations or waypoints (such as a restaurant, store, other vendor location, point of interest, etc.) in navigation information provided to an occupant, such as a driver, or group of occupants via the user interface 920; publishing occupant- or vehicle-related information, via a social network, to associated or selected associates of the each of the occupant(s); collecting occupant- and vehicle-related information (including any of the information described above) and forwarding the collected information to a vendor server, map database manager 812, and/or vehicle database manager 820; and presenting advertisement information, such as web pages and hyperlinks, from a vendor server 808 or vehicle database manager 820 to an occupant.

Figure 11:
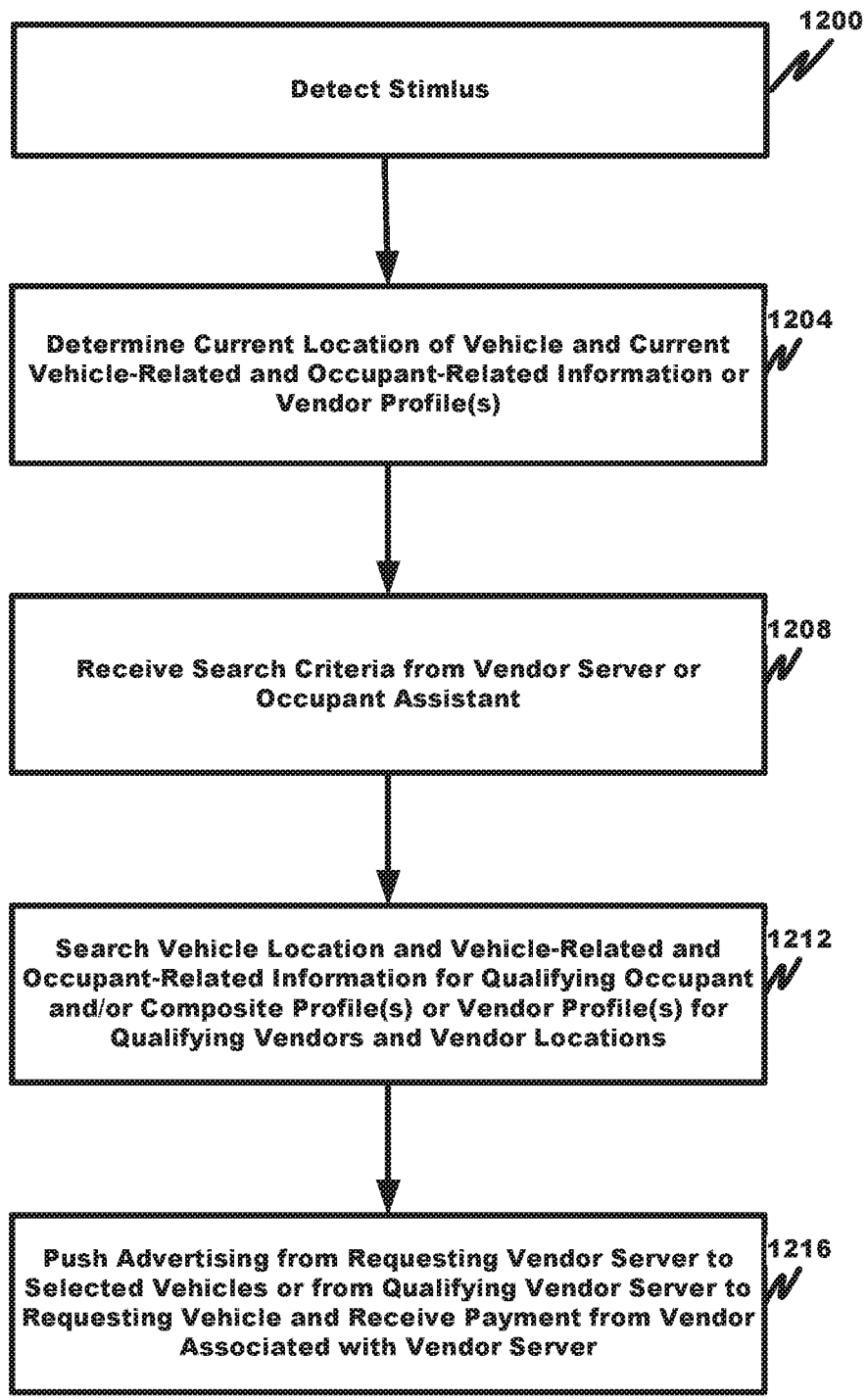
FIG. 11 is a flow chart associated with one or more embodiments presented herein.

With reference to FIG. 11, the vehicle database manager 820, in step 1200, detects a stimulus, such as for example any of the stimulus set forth above, a request for advertising targets received from a vendor server, a request for vendor information received from the occupant assistant 904, and other stimuli, and commences execution of the instructions.

In step 1204, the vehicle database manager determines from the vehicle database 824 and/or from the automatic vehicle location system 908 of the vehicle 120 the current geographical location of the vehicle 120 and the current vehicle-related and occupant-related information, including individual vehicle occupant profiles and/or a composite vehicle occupant profile, depending on the application, or vendor profiles depending on whether the request is received from a vendor server or occupant assistant.

In step 1208, the vehicle database manager 820 receives search criteria from one or more of the vendor server(s) 808A-N or occupant assistant.

In step 1212, the vehicle database manager 820 searches the vehicle location and vehicle-related and occupant-related information for qualifying occupant and/or composite profile(s) when the request is from a vendor server or one or more vendor profiles for qualifying vendors and qualifying vendor locations when the request is from the occupant assistant. "Qualifying" is deemed to exist when a search target satisfies the search criteria specified by the vendor or occupant assistant, as the case may be.

In step 1216, the vehicle database manager pushes advertising content from the requesting vendor server to qualifying or selected vehicles or from qualifying vendor server(s) to the requesting vehicle. When appropriate, the vehicle database manager receives a payment from the vendor server corresponding to the advertising content for pushing the advertising content to the vehicle, such payment terms discussed above in more detail.

Figure 12:
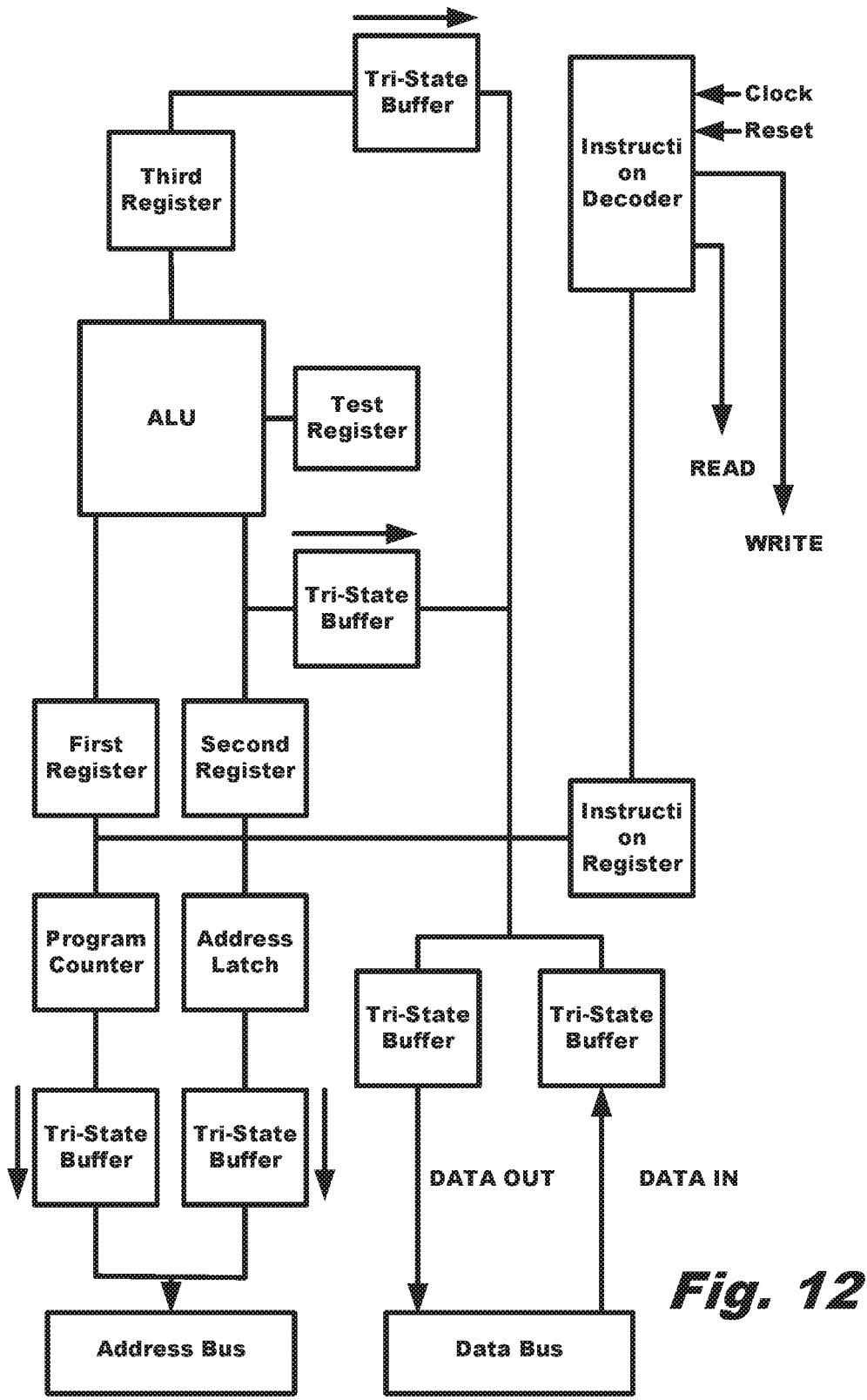
FIG. 12 is a block diagram of a computing system associated with one or more components described herein.

With reference to FIG. 12, the logical instructions are executed by an arithmetic/logic unit ("ALU"), which performs mathematical operations, such as addition, subtraction, multiplication, and division, machine instructions, an address bus (that sends an address to memory), a data bus (that can send data to memory or receive data from memory), a read and write line to tell the memory whether to set or get the addressed location, a clock line that enables a clock pulse to sequence the processor, and a reset line that resets the program counter to zero or another value and restarts execution. The arithmetic/logic unit can be a floating point processor that performs operations on floating point numbers. The occupant assistant 904, vehicle database manager 820, and/or map database manager 812 further includes first, second, and third registers that are typically configured from flip-flops, an address latch, a program counter (which can increment by "1" and reset to "0"), a test register to hold values from comparisons performed in the arithmetic/logic unit (such as comparisons in steps 1020, 1112, 1116, and 1212), plural tri-state buffers to pass a "1" or "0" or disconnect its output (thereby allowing multiple outputs to connect to a wire but only one of them to actually drive a "1" or "0" into the line), and an instruction register and decoder to control other components. Control lines, in the occupant assistant 904, vehicle database manager 820, and/or map database manager 812, from the instruction decoder can: command the first register to latch the value currently on the data bus, command the second register to latch the value currently on the data bus, command the third register to latch the value currently output by the ALU, command the program counter register to latch the value currently on the data bus, command the address register to latch the value currently on the data bus, command the instruction register to latch the value currently on the data bus, command the program counter to increment, command the program counter to reset to zero, activate any of the plural tri-state buffers (plural separate lines), command the ALU what operation to perform, command the test register to latch the ALU's test bits, activate the read line, and activate the write line. Bits from the test register and clock line as well as the bits from the instruction register come into the instruction decoder. Hardware similar or identical to that of FIG. 12 is in each of the occupant assistant 904, vehicle database manager 820 and/or map database manager 812 for executing the instructions of FIGS. 9-11. The ALU executes instructions for a random or pseudo-random number generation algorithm and generates the recipient identifier using the appropriate seed values.

Any of the steps, functions, and operations discussed herein can be performed continuously and automatically.

The exemplary systems and methods of this disclosure have been described in relation to vehicle systems and electric vehicles. However, to avoid unnecessarily obscuring the present disclosure, the preceding description omits a number of known structures and devices. This omission is not to be construed as a limitation of the scope of the claimed disclosure. Specific details are set forth to provide an understanding of the present disclosure. It should, however, be appreciated that the present disclosure may be practiced in a variety of ways beyond the specific detail set forth herein.

Furthermore, while the exemplary embodiments illustrated herein show the various components of the system collocated, certain components of the system can be located remotely, at distant portions of a distributed network, such as a LAN and/or the Internet, or within a dedicated system. Thus, it should be appreciated, that the components of the system can be combined into one or more devices, such as a server, communication device, or collocated on a particular node of a distributed network, such as an analog and/or digital telecommunications network, a packet-switched network, or a circuit-switched network. It will be appreciated from the preceding description, and for reasons of computational efficiency, that the components of the system can be arranged at any location within a distributed network of components without affecting the operation of the system.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire, and fiber optics, and may take the form of acoustic or light waves, such as those generated during radio-wave and infra-red data communications.

While the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

In yet another embodiment, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the present disclosure includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as a program embedded on a personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the embodiments with reference to particular standards and protocols, the disclosure is not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

Embodiments include a vehicle comprising:
a vehicle interior for receiving one or more occupants;
a powertrain to transmit power from a power source to an electric motor to propel the vehicle;
a user interface to receive input from an occupant and provide output to the occupant;
a plurality of sensors to sense information related to occupants;
an automatic vehicle location system to determine a current spatial location of the vehicle;
a computer readable medium to store a composite occupant profile; and
a microprocessor, coupled to the user interface, plurality of sensors, automatic vehicle location system, and computer readable medium, to:
determine that the vehicle interior comprises plural occupants;
identify the plural occupants;
based on the driving behavior of the vehicle, create a composite occupant profile associated with the group of plural occupants, the composite occupant profile comprising the identities of the plural occupants and group preferences for various vendor products or services; and
based on the composite occupant profile and received inputs from the user interface, automatic vehicle location system, and plurality of sensors, one or more of: (a) propose one or more vendor products or services for the group of occupants; (b) publish the one or more vendor products or services selected by the group of occupants, via a social network, to associated or selected associates of one or more of the occupants in the group; and (c) present advertisement information from a vendor server associated with the proposed or selected one or more vendor products or services to one or more of the occupants in the group.

Embodiments include a method that includes the steps:
determining, by a microprocessor, that the vehicle interior comprises plural occupants;
identifying, by the microprocessor, the plural occupants;
based on the driving behavior of the vehicle, creating, by the microprocessor, a composite occupant profile associated with the group of plural occupants, the composite occupant profile comprising the identities of the plural occupants and group preferences for various vendor products or services; and based on the composite occupant profile and received inputs from a user interface, an automatic vehicle location system, and a plurality of sensors in the vehicle, the microprocessor one or more of: (a) proposing one or more vendor products or services for the group of occupants; (b) publishing the one or more vendor products or services selected by the group of occupants, via a social network, to associated or selected associates of one or more of the occupants in the group; and (c) presenting advertisement information from a vendor server associated with the proposed or selected one or more vendor products or services to one or more of the occupants in the group.

Aspects of the above vehicle or method can include one or more of: the driving behavior being one or more of current or historical user driving behavior, historical route driven by the vehicle, destination of the vehicle, and waypoints of the vehicle; the driving behavior of the vehicle being attributed to the group of occupants; the plurality of sensors comprising a plurality of: a camera to capture images of the occupants in the vehicle interior, a camera to capture images of objects outside the vehicle, a seat belt sensor to determine a seat belt setting, a seat weight sensor to determine a weight of a seated occupant, a microphone to capture speech of the plurality of occupants, and a portable computing device of one or more of the occupants to sense interaction of the one or more of the occupants with the portable computing device; and the composite profile comprising, for each occupant in the group, the occupant's identity and the occupant's age or the occupant's biometric information and, for the group, visitation and/or transaction history with one or more vendors.

Aspects of the above vehicle or method can include the composite profile comprising, for each occupant in the occupant group, a role value indicating a role the corresponding occupant plays in a group decision.

Aspects of the above vehicle or method can include one or more of: the microprocessor proposing one or more vendor products or services for the group of occupants and the proposed one or more vendor products being proposed based on a number of group members, ages of the group members, and sexes of the group members and a need, specification, or availability of a product or service offered by a vendor.

Aspects of the above vehicle or method can include the microprocessor publishing the one or more vendor products or services selected by the group of occupants, via a social network, to associated or selected associates of one or more of the occupants in the group.

Aspects of the above vehicle or method can include the microprocessor presenting advertisement information from a vendor server associated with the proposed or selected one or more vendor products or services to one or more of the occupants in the group and the advertisement information being associated with a vendor product or service located within a selected spatial range of a current vehicle location.

Aspects of the above vehicle or method can include the composite profile being created by combining like preference field values in the individual profiles of the occupants in the group using one or more of a role value for each occupant in the group for that preference field, an unweighted average of the field values of the group occupants for a selected preference, a mode of the field values of the group occupants for a selected preference, and a median of the field values of the group occupants for a selected preference.

Aspects of the above vehicle or method can include the composite profile being created by combining like preference field values in the individual profiles of the occupants in the group using predictive analytics.

Embodiments include a method that includes the steps:
receiving, by a computer server, a request to provide advertising information to a vehicle;
determining, by the computer server, a current location of plural vehicles comprising the vehicle and current vehicle related and occupant-related information associated with occupants of the plurality of vehicles;
receiving, by the computer server, search criteria from a vendor server or the vehicle;
searching, by the computer server and in accordance with the search criteria, the determined current locations and the vehicle-related and occupant-related information associated with the occupants of the plurality of vehicles or plural vendor profiles including vendor locations; and
based on the searching, providing, by the computer server, to the vehicle selected advertising content responsive to the search criteria.

Aspects of the above vehicle or method can include the search criteria beings received from the vendor server and the computer server searching the determined current locations and the vehicle-related and occupant-related information to determine the vehicles in the plurality of vehicles to receive the advertising content from the vendor server and not receive the advertising content from the vendor server.

Aspects of the above vehicle or method can include the search criteria being received from the vehicle and the computer server searching the plural vendor profiles to determine vendor locations in spatial proximity to the vehicle and meeting a need, specification or requirement of the vehicle occupants and wherein the advertising content is associated with the determined vendor locations.

Aspects of the above vehicle or method can include the computer server causing payment to be made by or an invoice to be received from a vendor server providing the advertising content in exchange for the computer server providing the advertising content to the vehicle.

Any one or more of the aspects/embodiments as substantially disclosed herein.

Any one or more of the aspects/embodiments as substantially disclosed herein optionally in combination with any one or more other aspects/embodiments as substantially disclosed herein.

One or means adapted to perform any one or more of the above aspects/embodiments as substantially disclosed herein.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an embodiment that is entirely hardware, an embodiment that is entirely software (including firmware, resident software, micro-code, etc.) or an embodiment combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably and include any type of methodology, process, mathematical operation or technique.

The term "electric vehicle" (EV), also referred to herein as an electric drive vehicle, may use one or more electric motors or traction motors for propulsion. An electric vehicle may be powered through a collector system by electricity from off-vehicle sources, or may be self-contained with a battery or generator to convert fuel to electricity. An electric vehicle generally includes a rechargeable electricity storage system (RESS) (also called Full Electric Vehicles (FEV)). Power storage methods may include: chemical energy stored on the vehicle in on-board batteries (e.g., battery electric vehicle or BEV), on board kinetic energy storage (e.g., flywheels), and/or static energy (e.g., by on-board double-layer capacitors). Batteries, electric double-layer capacitors, and flywheel energy storage may be forms of rechargeable on-board electrical storage.

The term "hybrid electric vehicle" refers to a vehicle that may combine a conventional (usually fossil fuel-powered) powertrain with some form of electric propulsion. Most hybrid electric vehicles combine a conventional internal combustion engine (ICE) propulsion system with an electric propulsion system (hybrid vehicle drivetrain). In parallel hybrids, the ICE and the electric motor are both connected to the mechanical transmission and can simultaneously transmit power to drive the wheels, usually through a conventional transmission. In series hybrids, only the electric motor drives the drivetrain, and a smaller ICE works as a generator to power the electric motor or to recharge the batteries. Power-split hybrids combine series and parallel characteristics. A full hybrid, sometimes also called a strong hybrid, is a vehicle that can run on just the engine, just the batteries, or a combination of both. A mid hybrid is a vehicle that cannot be driven solely on its electric motor, because the electric motor does not have enough power to propel the vehicle on its own.

The term "rechargeable electric vehicle" or "REV" refers to a vehicle with on board rechargeable energy storage, including electric vehicles and hybrid electric vehicles.

What is claimed is:

1. A vehicle, comprising:
a vehicle interior for receiving one or more occupants;
a powertrain to transmit power from a power source to an electric motor to propel the vehicle;
a user interface to receive input from an occupant and provide output to the occupant;
a plurality of sensors to sense information related to occupants;
an automatic vehicle location system to determine a current spatial location of the vehicle;
a computer readable medium to store a composite occupant profile; and
a microprocessor, coupled to the user interface, plurality of sensors, automatic vehicle location system, and computer readable medium, to:
determine that the vehicle interior comprises a group of plural occupants;
identify each occupant of the group of plural occupants;
based on individual profiles of the group of plural occupants, create a composite occupant profile that represents the group of plural occupants, the composite occupant profile comprising an identity of each occupant of the group of plural occupants and group preferences for various vendor products or services, wherein each occupant of the group of plural occupants has a corresponding individual occupant profile, each individual occupant profile comprising individual preference values, wherein the composite occupant profile and the group preferences are created by combining, for a selected preference, a preference value for the selected preference retrieved from the individual preference values for each occupant using one or more of a role value for each occupant of the group of plural occupants, an unweighted average of the individual preference values of each occupant of the group of plural occupants for the selected preference, a mode of the individual preference values of each occupant of the group of plural occupants for the selected preference, and a median of the individual preference values of each occupant of the group of plural occupants for the selected preference; and
based on the composite occupant profile and received inputs from the user interface, automatic vehicle location system, and plurality of sensors, one or more of: (a) propose one or more vendor products or services for the group of plural occupants; (b) publish the one or more vendor products or services selected by the group of plural occupants, via a social network, to associated or selected associates of one or more of the occupants in the group of plural occupants; and (c) present advertisement information from a vendor server associated with the proposed or selected one or more vendor products or services to one or more of the occupants in the group of plural occupants.

2. The vehicle of claim 1, wherein the composite occupant profile comprises plural preference fields, wherein a preference value of at least one of the plural preference fields in the composite occupant profile is based on a preference value in an individual occupant profile of an occupant of a different vehicle and not currently an occupant of the vehicle, wherein creating the composite occupant profile is based on a driving behavior of the vehicle, wherein the driving behavior is one or more of current or historical user driving behavior, historical route driven by the vehicle, destination of the vehicle, and waypoints of the vehicle, wherein the driving behavior of the vehicle is attributed to the group of plural occupants, wherein the plurality of sensors comprise a plurality of: a camera to capture images of the occupants in the vehicle interior, a camera to capture images of objects outside the vehicle, a seat belt sensor to determine a seat belt setting, a seat weight sensor to determine a weight of a seated occupant, a microphone to capture speech of the group of plural occupants, and a portable computing device of at least one of the group of plural occupants to sense interaction of the at least one of the group of plural occupants with the portable computing device, and wherein the composite occupant profile comprises, for each occupant of the group of plural occupants, an age or biometric information for each occupant and, for the group of plural occupants, visitation and/or transaction history with one or more vendors.

3. The vehicle of claim 1, wherein the microprocessor provides information in the composite occupant profile to multiple vendor servers of multiple vendors, wherein the composite occupant profile comprises, for each occupant in the group of plural occupants the role value indicating a role a corresponding occupant plays in a group decision, each occupant of the group of plural occupants having a different role value, wherein, in response to providing the information, the microprocessor receives multiple vendor responses from the multiple vendors, assigns a compliance score to each of the multiple vendor responses, the compliance score indicating a degree of compliance of a respective vendor response with one or more of an occupant preference and an attractiveness of the respective vendor response to a need, specification, or requirement of the composite occupant profile, filters the multiple vendor responses based on the assigned compliance scores, and provides a subset of the multiple vendor responses to at least one occupant of the group of plural occupants.

4. The vehicle of claim 1, wherein the microprocessor directly or indirectly provides vehicle occupant information in the composite occupant profile and current vehicle location to the vendor server, wherein the microprocessor proposes one or more vendor products or services for the group of plural occupants, wherein the microprocessor provides to an occupant of the group of plural occupants a plurality of vendor hours of operation, available product and/or service types, available product and/or service prices, available product and/or service specifications or requirements, and geographical location of a respective vendor, wherein the microprocessor provides to the occupant a geographic data file comprising the geographic location of the respective vendor, wherein the plurality of vendor hours of operation, available product and/or service types, available product and/or service prices, available product and/or service specifications or requirements, and geographical location of the respective vendor are cross-referenced by a function-specific referencing table and/or generic reference features or attributes of the geographic data file, and wherein the proposed one or more vendor products is proposed based on a number of members in the group of plural occupants, ages of the members in the group of plural occupants, and sexes of the members in the group of plural occupants and a need, specification, or availability of a product or service offered by a vendor.

5. The vehicle of claim 1, wherein the microprocessor publishes the one or more vendor products or services selected by the group of plural occupants, via the social network, to associated or selected associates of one or more of the occupants in the group of plural occupants and the publication comprises a plurality of vendor hours of operation, available product and/or service types, available product and/or service prices, available product and/or service specifications or requirements, and geographical location of a respective vendor.

6. The vehicle of claim 1, wherein the microprocessor directly or indirectly provides vehicle occupant information in the composite occupant profile and current vehicle location to the vendor server, wherein the microprocessor presents advertisement information from the vendor server associated with the proposed or selected one or more vendor products or services to one or more of the occupants in the group of plural occupants, wherein the microprocessor provides to an occupant a plurality of vendor hours of operation, available product and/or service types, available product and/or service prices, available product and/or service specifications or requirements, and geographical location of a respective vendor, wherein the microprocessor provides to the occupant a geographic data file comprising the geographic location of the respective vendor, wherein the plurality of vendor hours of operation, available product and/or service types, available product and/or service prices, available product and/or service specifications or requirements, and geographical location of the respective vendor are cross-referenced by a function-specific referencing table and/or generic reference features or attributes of the geographic data file, and wherein the advertisement information is associated with a vendor product or service located within a selected spatial range of a current vehicle location.

7. The vehicle of claim 1, wherein the composite occupant profile comprises plural preference fields, wherein, when the microprocessor determines that a selected preference field in each individual occupant profile of two or more occupants comprise of the group of plural occupants comprises a conflicting value, the microprocessor uses, for the selected preference field value in the composite occupant profile, one or more of a most frequently occurring value for the selected preference, the value of the selected preference field in the individual occupant profile having a highest role ranking and multiple, different values in the individual occupant profiles, each of which is a source of a stimulus or suggestion or recommendation to the two or more occupants of the group of plural occupants.

8. The vehicle of claim 1, wherein the composite profile is created by combining like preference field values in the individual occupant profiles of the group of plural occupants using one or more of (i) predictive analytics comprising one or more of a regression technique, linear regression model, discrete choice model, logistic regression, multinomial logistic regression, probit regression, time series model, survival or duration analysis, classification and regression tree, multivariate adaptive regression spline, machine learning technique, neural network, multilayer perception, radial basis function, support vector machine, Nave Bayes, k-nearest neighbor, and geospatial predictive modeling and (ii) behavioral segmentation, in which the microprocessor divides occupants of multiple different vehicles into groups or classes based on selected parameters of behavior using one or more of an objective and non-objective segmentation methodology to maximize a difference among segments with regards to each selected behavior parameter.

9. A method, comprising:
  determining, by a microprocessor, that a vehicle interior comprises a group of plural occupants;
  identifying, by the microprocessor, each occupant of the group of plural occupants;
  based on individual profiles of the group of plural occupants, creating, by the microprocessor, a composite occupant profile that represents the group of plural occupants, the composite occupant profile comprising an identity of each occupant of the group of plural occupants and group preferences for various vendor products or services, wherein each occupant of the group of plural occupants has a corresponding individual occupant profile, each individual occupant profile comprising individual preference values, wherein the composite occupant profile and the group preferences are created by combining, for a selected preference, a preference value for the selected preference retrieved from the individual preference values for each occupant using one or more of a role value for each occupant of the group of plural occupants, an unweighted average of the individual preference values of each occupant of the group of plural occupants for the selected preference, a mode of the individual preference values of each occupant of the group of plural occupants for the selected preference, and a median of the individual preference values of each occupant of the group of plural occupants for the selected preference; and
  based on the composite occupant profile and received inputs from a user interface, an automatic vehicle location system, and a plurality of sensors in the vehicle, one or more of: (a) proposing, by the microprocessor, one or more vendor products or services for the group of plural occupants; (b) publishing, by the microprocessor, the one or more vendor products or services selected by the group of plural occupants, via a social network, to associated or selected associates of one or more of the occupants in the group; and (c) presenting, by the microprocessor, advertisement information from a vendor server associated with the proposed or selected one or more vendor products or services to one or more of the occupants in the group of plural occupants.

10. The method of claim 9, wherein the composite occupant profile comprises plural preference fields, wherein a preference value of at least one of the plural preference fields in the composite occupant profile is based on a preference value in an individual occupant profile of an occupant of a different vehicle and not currently an occupant of the vehicle, wherein creating the composite occupant profile is based on a driving behavior of the vehicle, wherein the driving behavior is one or more of current or historical user driving behavior, historical route driven by the vehicle, destination of the vehicle, and waypoints of the vehicle, wherein the driving behavior of the vehicle is attributed to the group of plural occupants, wherein the plurality of sensors comprise a plurality of: a camera to capture images of the occupants in the vehicle interior, a camera to capture images of objects outside the vehicle, a seat belt sensor to determine a seat belt setting, a seat weight sensor to determine a weight of a seated occupant, a microphone to capture speech of the group of plural occupants, and a portable computing device of at least one of the group of plural occupants to sense interaction of the at least one of the group of plural occupants with the portable computing device, and wherein the composite occupant profile comprises, for each occupant of the group of plural occupants, an age or biometric information for each occupant and, for the group of plural occupants, visitation and/or transaction history with one or more vendors.

11. The method of claim 9, further comprising:
providing, by the microprocessor, information in the composite occupant profile to multiple vendor servers of multiple vendors, wherein the composite occupant profile comprises, for each occupant in the group of plural occupants, the role value indicating a role a corresponding occupant plays in a group decision, each occupant of the group of plural occupants having a different role value;
receiving, by the microprocessor and in response to providing the information, multiple vendor responses from the multiple;
assigning, by the microprocessor, a compliance score to each of the multiple vendor responses received, the compliance score indicating a degree of compliance of the respective vendor response with one or more of an occupant preference and an attractiveness of the respective vendor response to a need, specification or requirement of the composite occupant profile;
filtering, by the microprocessor, the multiple vendor responses based on the assigned compliance scores; and
providing, by the microprocessor and based on the filtering, a subset of the multiple vendor responses to at least one occupant of the group of plural occupants.

12. The method of claim 9, wherein the microprocessor directly or indirectly provides vehicle occupant information in the composite occupant profile and current vehicle location to the vendor server, wherein the microprocessor proposes one or more vendor products or services for the group of plural occupants, wherein the microprocessor provides to an occupant of the group of plural occupants a plurality of vendor hours of operation, available product and/or service types, available product and/or service prices, available product and/or service specifications or requirements, and geographical location of a respective vendor, wherein the microprocessor provides to the occupant a geographic data file comprising the geographic location of the respective vendor, wherein the plurality of vendor hours of operation, available product and/or service types, available product and/or service prices, available product and/or service specifications or requirements, and geographical location of the respective vendor are cross-referenced by a function-specific referencing table and/or generic reference features or attributes of the geographic data file, and wherein the proposed one or more vendor products is proposed based on a number of members in the group of plural occupants, ages of the members in the group of plural occupants, and sexes of the members in the group of plural occupants and a need, specification, or availability of a product or service offered by a vendor.

13. The method of claim 9, further comprising:
publishing, by the microprocessor, the one or more vendor products or services selected by the group of plural occupants, via the social network, to associated or selected associates of one or more of the occupants in the group of plural occupants and the publication comprises a plurality of vendor hours of operation, available product and/or service types, available product and/or service prices, available product and/or service specifications or requirements, and geographical location of a respective vendor.

14. The method of claim 9, further comprising:
providing, by the microprocessor directly or indirectly, vehicle occupant information in the composite occupant profile and current vehicle location to the vendor server;
presenting, by the microprocessor, advertisement information from the vendor server associated with the proposed or selected one or more vendor products or services to one or more of the occupants in the group of plural occupants;
providing, by the microprocessor, to an occupant a plurality of vendor hours of operation, available product and/or service types, available product and/or service prices, available product and/or service specifications or requirements, and geographical location of a respective vendor; and
providing, by the microprocessor, to the occupant a geographic data file comprising the geographic location of the respective vendor, wherein the plurality of vendor hours of operation, available product and/or service types, available product and/or service prices, available product and/or service specifications or requirements, and geographical location of the respective vendor are cross-referenced by a function-specific referencing table and/or generic reference features or attributes of the geographic data file, and wherein the advertisement information is associated with a vendor product or service located within a selected spatial range of a current vehicle location.

15. The method of claim 9, further comprising:
determining, by the microprocessor, that a selected preference field in each individual occupant profile of two or more occupants of the group of plural occupants comprises a conflicting value;
using, by the microprocessor, for the selected preference field value in the composite occupant profile, one or more of a most frequently occurring value for the selected preference, the value of the selected preference in the individual occupant profile having a highest role ranking and multiple, different values in the individual occupant profiles, each of which is a source of a stimulus or suggestion or recommendation to the two or more occupants of the group of plural occupants.

16. The method of claim 9, wherein the composite occupant profile is created by the microprocessor combining like preference field values in the individual occupant profiles of the group of plural occupants using one or more of (i)

predictive analytics comprising one or more of a regression technique, linear regression model, discrete choice model, logistic regression, multinomial logistic regression, probit regression, time series model, survival or duration analysis, classification and regression tree, multivariate adaptive regression spline, machine learning technique, neural network, multilayer perception, radial basis function, support vector machine, Naïve Bayes, k-nearest neighbor, and geospatial predictive modeling and (ii) behavioral segmentation, in which the microprocessor divides occupants of multiple different vehicles into groups or classes based on selected parameters of behavior using one or more of an objective and non-objective segmentation methodology to maximize a difference among segments with regards to each selected behavior parameter.

* * * * *

UNITED STATES PATENT AND TRADEMARK OFFICE
CERTIFICATE OF CORRECTION

PATENT NO. : 10,515,390 B2
APPLICATION NO. : 15/393010
DATED : December 24, 2019
INVENTOR(S) : Christopher F. Pouliot Page 1 of 1

It is certified that error appears in the above-identified patent and that said Letters Patent is hereby corrected as shown below:

In the Claims

Claim 3, Column 26, Line 48, insert a --,-- after "the group of plural occupants" therein.
Claim 7, Column 27, Line 60, delete "comprise" before the phrase "of the group" therein.
Claim 7, Column 27, Line 65, delete "field" therein.
Claim 8, Column 28, Line 14, delete "Nave" and insert --Naïve-- therein.

Signed and Sealed this
Tenth Day of March, 2020

Andrei Iancu
*Director of the United States Patent and Trademark Office*